(12) United States Patent
Tabaru et al.

(10) Patent No.: US 8,647,276 B2
(45) Date of Patent: Feb. 11, 2014

(54) ULTRASONIC DIAGNOSTIC DEVICE

(75) Inventors: Marie Tabaru, Hino (JP); Takashi Azuma, Sagamihara (JP); Kunio Hashiba, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 0 days.

(21) Appl. No.: 13/386,184

(22) PCT Filed: Aug. 4, 2010

(86) PCT No.: PCT/JP2010/063223
§ 371 (c)(1),
(2), (4) Date: Jan. 20, 2012

(87) PCT Pub. No.: WO2011/027644
PCT Pub. Date: Mar. 10, 2011

(65) Prior Publication Data
US 2012/0136250 A1    May 31, 2012

(30) Foreign Application Priority Data

Sep. 4, 2009 (JP) ................. 2009-204234

(51) Int. Cl.
*A61B 8/00* (2006.01)
(52) U.S. Cl.
USPC ............. 600/449; 600/443; 600/437
(58) Field of Classification Search
USPC ................. 600/437–469
See application file for complete search history.

(56) References Cited

U.S. PATENT DOCUMENTS

| 5,606,971 A | 3/1997 | Sarvazyan |
| 5,810,731 A | 9/1998 | Sarvazyan et al. |
| 6,068,597 A | 5/2000 | Lin |

(Continued)

FOREIGN PATENT DOCUMENTS

| JP | 2006500089 | 1/2006 |
| JP | 2010-507428 | 3/2010 |

OTHER PUBLICATIONS

M. Tanter, et al., "Quantitative Assessment of Breast Lesion Viscoelasticity: Initial Clinical Results Using Supersonic Shear Imaging", Ultrasound in Med. & Biol., vol. 34, No. 9, pp. 1373-1386, 2008.

(Continued)

*Primary Examiner* — Sanjay Cattungal
(74) *Attorney, Agent, or Firm* — Brundidge & Stanger, P.C.

(57) ABSTRACT

In a radiation-pressure elastography technique for transmitting a ultrasound focused beam into a test object body and diagnosing the hardness thereof, it is required to consider high sensitivity and safety.
In the present invention, the focused beam is transmitted to two positions as a means for displacing a tissue and exciting a shear wave. In addition, time control is performed in such a manner that a transmit beam serves as a burst-chirp signal, and ultrasound waves are transmitted and received while sweeping a transmit frequency. On this occasion, when the distance between the two focused points and the transmit frequency become integral multiple of the wavelength, two waves interfere with each other, thereby obtaining a large amplitude. Furthermore, when the transmit frequency becomes equal to a resonance frequency peculiar to the tissue, the amplitude also becomes larger. Accordingly, a small intensity of transmit waveform enhances sensitivity. In addition, transmission using the burst-chirp signal facilitates widening of a bandwidth of the transmit frequency, enabling usage of a frequency highly sensitive for a target measurement site. Optional number of focused points and arbitrary positions thereof allow a wide area to be covered.

15 Claims, 23 Drawing Sheets

(56) References Cited

U.S. PATENT DOCUMENTS

| | | | | |
|---|---|---|---|---|
| 6,176,829 B1* | 1/2001 | Vilkomerson | | 600/443 |
| 6,334,846 B1* | 1/2002 | Ishibashi et al. | | 600/439 |
| 6,424,597 B1* | 7/2002 | Bolomey et al. | | 367/138 |
| 8,323,201 B2* | 12/2012 | Towfiq et al. | | 600/459 |
| 8,366,622 B2* | 2/2013 | Slayton et al. | | 600/439 |
| 2004/0068184 A1 | 4/2004 | Trahey et al. | | |
| 2005/0252295 A1 | 11/2005 | Fink et al. | | |
| 2008/0276709 A1 | 11/2008 | Bercoff et al. | | |
| 2012/0053468 A1* | 3/2012 | Griffin et al. | | 600/459 |

OTHER PUBLICATIONS

X. Zhang, et al., "Further Investigation of Ring Resonance in Estimation of Local Elasticity of Arteries", 2007 IEEE Ultrasonic Symposium, pp. 1717-1719.

H. Yamamoto, et al., "Estimation of the Dynamic Young's Modulus of Apple Flesh From the Natural Frequency of an Intact Apple", Rept. Natl. Food Res. Inst., No. 44, 20-25, 1984.

International Search Report and Written Opinion for PCT International Application No. PCT/2010/063223, mailed on Nov. 16, 2010.

* cited by examiner (a)

(b)

(a)

(b)

ULTRASONIC DIAGNOSTIC DEVICE

TECHNICAL FIELD

The present invention relates to an ultrasonic diagnostic device for detecting a difference in hardness inside a test object, by transmitting and receiving ultrasound (ultrasonic) waves.

BACKGROUND ART

As a method for diagnosing breast cancer, liver cirrhosis, vascular disorder, and the like, there is a method for diagnosing the hardness inside a test object based on ultrasound echo signals (elastography technique), the method substituting for palpation by a doctor. In the diagnosis of the hardness according to the elastography technique, an engaged person presses a probe against a surface of the test object and exerts compression thereon, thereby causing displacement in tissue inside the living body (hereinafter, this technique is referred to as a conventional method). According to echo signals from the tissue of the living body, before and after compressed by pressure, it is possible to estimate the displacement in the compressed direction and obtain strains corresponding to spatial differential information of the displacement. Furthermore, based on the strain and stress, a value relating to the hardness is calculated, for instance, Young's modulus. In the aforementioned conventional method, there is a problem that a target for imaging is limited to an organ that is located easily compressed from the body surface. By way of example, there exists a slip surface as an intervening layer between the body surface and the liver, and it is difficult to exert compression sufficient enough to cause displacement in the liver. Therefore, according to the conventional method, it is difficult to calculate the hardness inside the liver by the use of the elastography technique.

In view of the situation above, there is a technique that the inside of the test object is exposed to a focused beam of ultrasound waves, thereby applying radiation pressure to the inside of the test object, allowing a target tissue to be displaced while diminishing the influence of the intervening layer, and the hardness thereof is diagnosed. By way of example, such technique as described above includes the ARFI (Acoustic Radiation Force Imaging) described in the Patent Document 1 and the SSI (Supersonic Shear Imaging) described in the Non Patent Document 1. Those techniques estimate an amount of tissue displacement which occurs in a proceeding direction of the focused beam, so as to calculate the Young's modulus, or estimate a velocity of a shear wave which is produced according to the displacement, in the direction vertical to the proceeding direction of the focused beam, thereby calculating a shear elastic modulus. Since the shear elastic modulus covers a wider range of values possibly obtained depending on various types of tissue, relative to the Young's modulus, it is possible to expect more precise diagnosis. By using those techniques described above, there is an effect of reducing the influence of the intervening layer such as the slip surface described above, and additionally, since ultrasound waves generate displacement in the tissue, diagnosis with less dependence on manual procedure is expected.

On the other hand, the Non Patent Document 2 describes the possibility that the test object is exposed to two focused beams having different frequencies, receiving a beat signal being a difference of the frequencies, and the hardness of blood vessels can be diagnosed based on a peak value of a spectrum of the beat signal. The technique here assumes the shape of the blood vessel as a ring, and adopts that the natural vibration frequency of the ring depends on the Young's modulus.

PRIOR ART DOCUMENT

Patent Document

[Patent Document 1]
US-A-20040068184
[Non Patent Document 1]
M. Tanter, et al., Ultrasound in Med. & Biol., Vol. 34, No. 9, pp. 1373-1386, 2008
[Non Patent Document 2]
X. Zhang et al., Proc. of the 2007 IEEE Ultrasonics Symposium, pp. 1717-1719, 2007
[Non Patent Document 3]
H. Yamamoto and S. Haginuma, Rept. Natl. Food Res. Inst, No. 44 pp. 20-24, 1984

DISCLOSURE OF THE INVENTION

Problem to be Solved by the Invention

When the focused beam of the ultrasound waves is transmitted into the test object, acoustic energy generated inside the test object is large and it has a profound impact on the tissue of the living body. On the other hand, if safety is considered and the acoustic energy is made smaller, the displacement of the tissue is diminished, resulting in a reduction of penetration (shear-wave propagation distance). Accordingly, it is desired to achieve an imaging technique which is highly sensitive as well as considering safety.

Means to Solve the Problem

The present invention is directed to generation of displacement in tissue, allowing a shear wave produced along with the displacement to undergo excitation. For the purpose above, the present invention transmits a focused beam of ultrasound waves, assuming two spots in the tissue as focused points, respectively. On this occasion, the ultrasound waves are transmitted and received, along with sweeping a switching period ON and OFF, so that the focused beam for each focused point serves as a burst-chirp signal (which will be explained below in the description of the first embodiment). The ON timing and OFF timing of the focused beam directed to the two focused points alternately appear, and when the distance between the two focused points becomes (n+½) times longer than the wavelength $\lambda$ ("n" is a non-negative integer) that is determined by the switching period and the shear wave velocity peculiar to the tissue, the two waves interfere with each other and large amplitude is obtained. In addition, when the switching period agrees with a frequency peculiar to the hardness and the form of the tissue, there is an increase in amplitude. According to the means described above, the amount of displacement is magnified with small intensity of ultrasound waves. Consequently, it is possible to improve the sensitivity of the elastography imaging by the use of radiation pressure. In addition, transmission with the use of a burst-chirp signal facilitates expanding of a bandwidth of the switching period, and therefore, it is possible to make a wide search for the switching period that enables acquisition of high sensitivity at a measurement target site. The number of the focused points and the position thereof are optionally settable, thereby allowing coverage of a wide diagnosis domain.

Effect of the Invention

According to the present invention, a burst-chirp signal is used to cause interference between the shear waves produced by multiple focused ultrasound waves, thereby allowing a value of amplitude of the shear wave to be magnified. Therefore, this brings about enhancement of the displacement amount (hereinafter, also referred to as transmission sensitivity) of the tissue, with respect to the wave transmission to the tissue. In addition, multiple focused points are provided to disperse energy generated inside the test object, thereby achieving improvement of safety, from the viewpoint of both a thermal mode of action and a mechanical mode of action. Furthermore, transmission with the use of the burst-chirp signal allows expanding of a bandwidth of the switching period, and therefore, it is possible to transmit waves in the switching period that achieves acquisition of high transmission sensitivity at a measurement site, resulting in enhancement of robustness.

MODES FOR CARRYING OUT THE INVENTION

Figure 1:
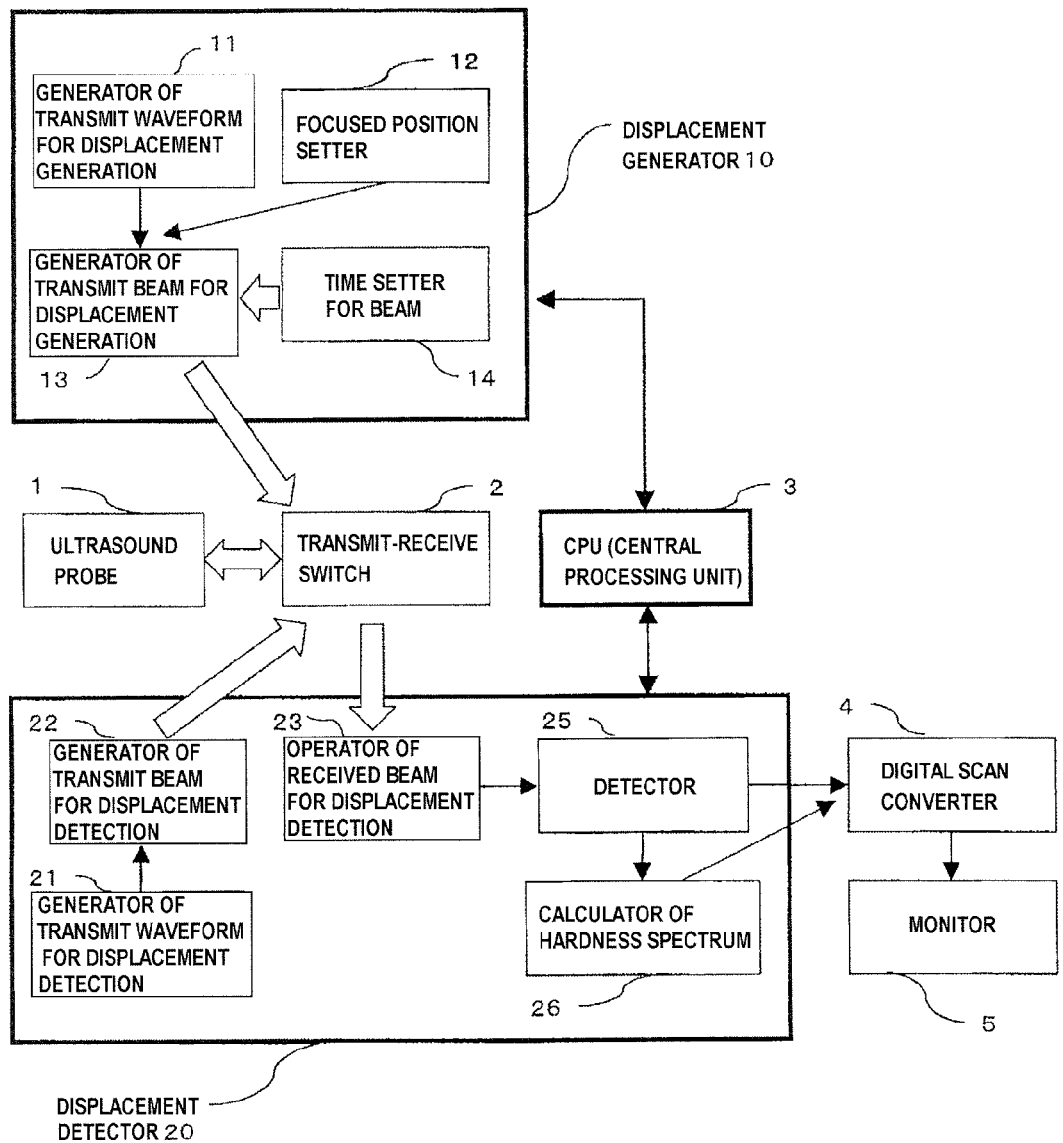
FIG. 1 is a block diagram showing a system configuration of an ultrasonic diagnostic device according to the first embodiment.

Hereinafter, embodiments of the present invention will be explained. FIG. 1 shows an overall configuration of an ultrasonic diagnostic device of the present embodiment. This ultrasonic diagnostic device is provided with an ultrasound probe 1 for transmitting and receiving an ultrasound beam to and from a test object not illustrated, a displacement generator 10 for generating displacement in the test object, a displacement detector 20 for detecting the displacement generated in the test object, a CPU (Central Processing Unit) 3 for controlling the displacement generator 10 and the displacement detector 20, a transmit-receive switch 2, and a digital scan converter 4.

The displacement generator 10 incorporates, a generator of transmit waveform for displacement generation 11, a focused position setter 12, a generator of transmit beam for displacement generation 13, and a time setter for beam 14. The displacement detector 20 incorporates, a generator of transmit waveform for displacement detection 21, a generator of transmit beam for displacement detection 22, an operator of received beam for displacement detection 23, a detector 25, and a calculator of hardness spectrum 26.

The ultrasound probe 1 is connected, via the transmit-receive switch 2, with the generator of transmit beam for displacement generation 13, the time setter for beam 14, the generator of transmit beam for displacement detection 22, and the operator of received beam for displacement detection 23. There are arranged multiple devices in the ultrasound probe 1, the devices converting an electric signal into an ultrasound signal.

Firstly, an explanation will be made as to the operation of each element in the displacement generator 10. The generator of transmit waveform for displacement generation 11 generates a predetermined transmit waveform for displacement generation. The generator of transmit beam for displacement generation 13 uses the transmit waveform generated by the generator of transmit waveform for displacement generation 11, to generate a transmit signal to be transferred, with respect to each of the devices in the ultrasound probe 1. On this occasion, the generator of transmit beam for displacement generation 13 assigns a predetermined delay time and weights to the transmit signal for each device, so as to generate the transmit signal in such a manner that an ultrasound beam transmitted from the ultrasound probe 1 is focused onto a position which is set by the focused position setter 12. The transmit signal (electric signal) from the generator of transmit beam for displacement generation 13 is transferred to the ultrasound probe 1. The ultrasound probe 1 converts the transmit signal into an ultrasound signal. Accordingly, the test object not illustrated is exposed to the ultrasound beam for generating the displacement. On this occasion, the focused position setter 12 sets predetermined multiple focused points (focused points F1 and F2), and the time setter for beam 14 sets an exposure start time and an exposure end time of the ultrasound beam for displacement generation, in such a manner that multiple focused points (focused points F1 and F2) are repeatedly exposed to the ultrasound beam alternately at a predetermined switching period (burst-chirp signal). The CPU (Central Processing Unit) 3 controls the operation of each element in the displacement generator 10.

Next, an explanation will be made as to each element of the displacement detector 20. After exposure of the ultrasound beam for displacement generation, the test object is exposed to an ultrasound beam for detecting displacement in order to detect the displacement of the tissue within the test object. Similar to the ultrasound beam for displacement generation, the generator of transmit beam for displacement detection 22 uses a waveform generated by the generator of transmit waveform for displacement detection 21 to generate a transmit signal to be transferred with respect to each device of the ultrasound probe 1. On this occasion, the generator of transmit beam for displacement detection 22 assigns a predetermined delay time and weights to the transmit signal with respect to each device, so as to generate the transmit signal in such a manner that an ultrasound beam for displacement detection transmitted from the ultrasound probe 1 is focused onto a desired point for displacement detection. The ultrasound probe 1 receives this transmit signal, and allows the desired point for displacement detection to be exposed to the ultrasound beam for displacement detection.

A part of the exposure of ultrasound beam for displacement detection undergoes reflection within the test object, then turns into an echo signal, and returns to the probe 1. The echo signal is converted into an electric signal in the ultrasound probe 1. The operator of received beam for displacement detection 23 acquires the receive signal from the ultrasound probe 1, and carries out an operation of phasing and adding for beam forming. An output from the operator of received beam for displacement detection 23 is subjected to a signal control in the detector 25, such as an envelope detection, log compression, filtering by a band pass filter, and a gain control, and thereafter, the calculator of hardness spectrum 26 calculates a value relating to the hardness. Outputs from the detector 25 and the calculator of hardness spectrum 26 are converted into an image signal in the scan converter 4, and displayed in the monitor 5, in the form of a numerical value or an image representing the hardness. The CPU (Central Processing Unit) 3 controls the operation of the displacement detector 20.

First Embodiment

Figure 2:
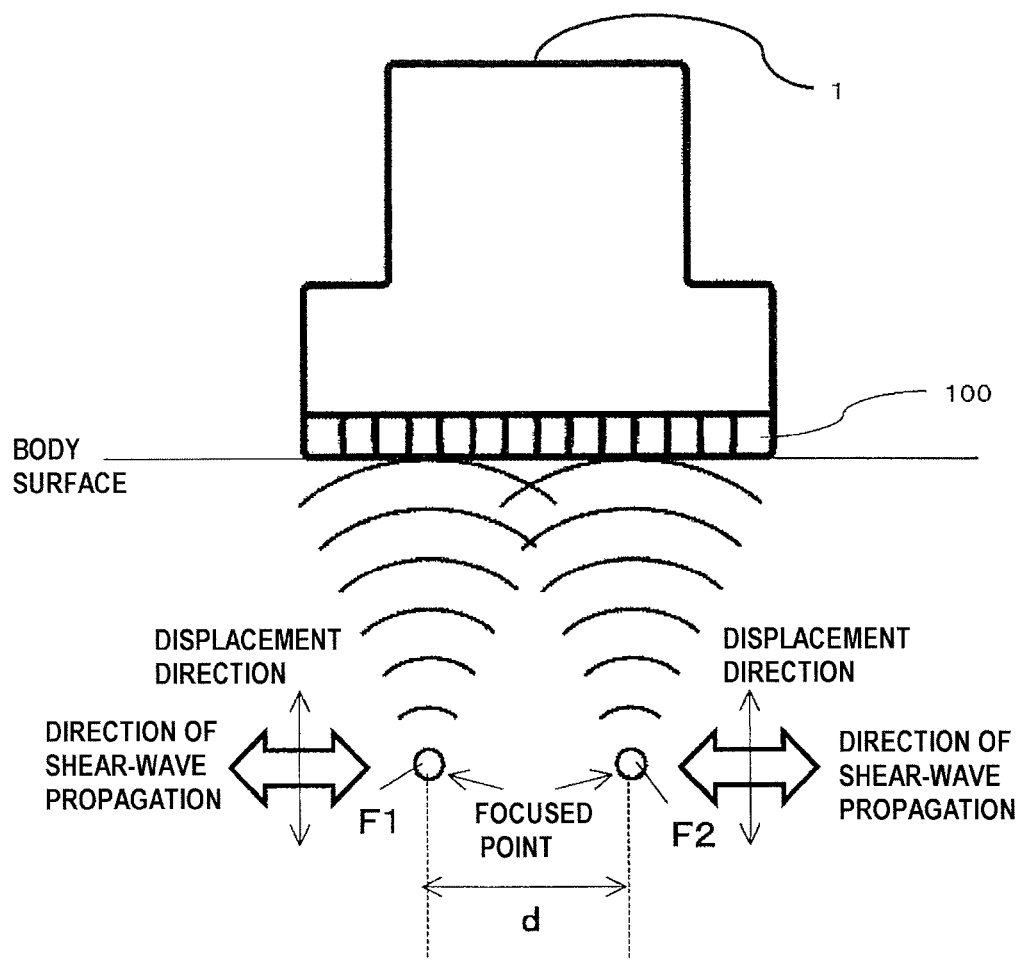
FIG. 2 illustrates a method of measurement using an ultrasound probe according to the first embodiment.
Figure 3:
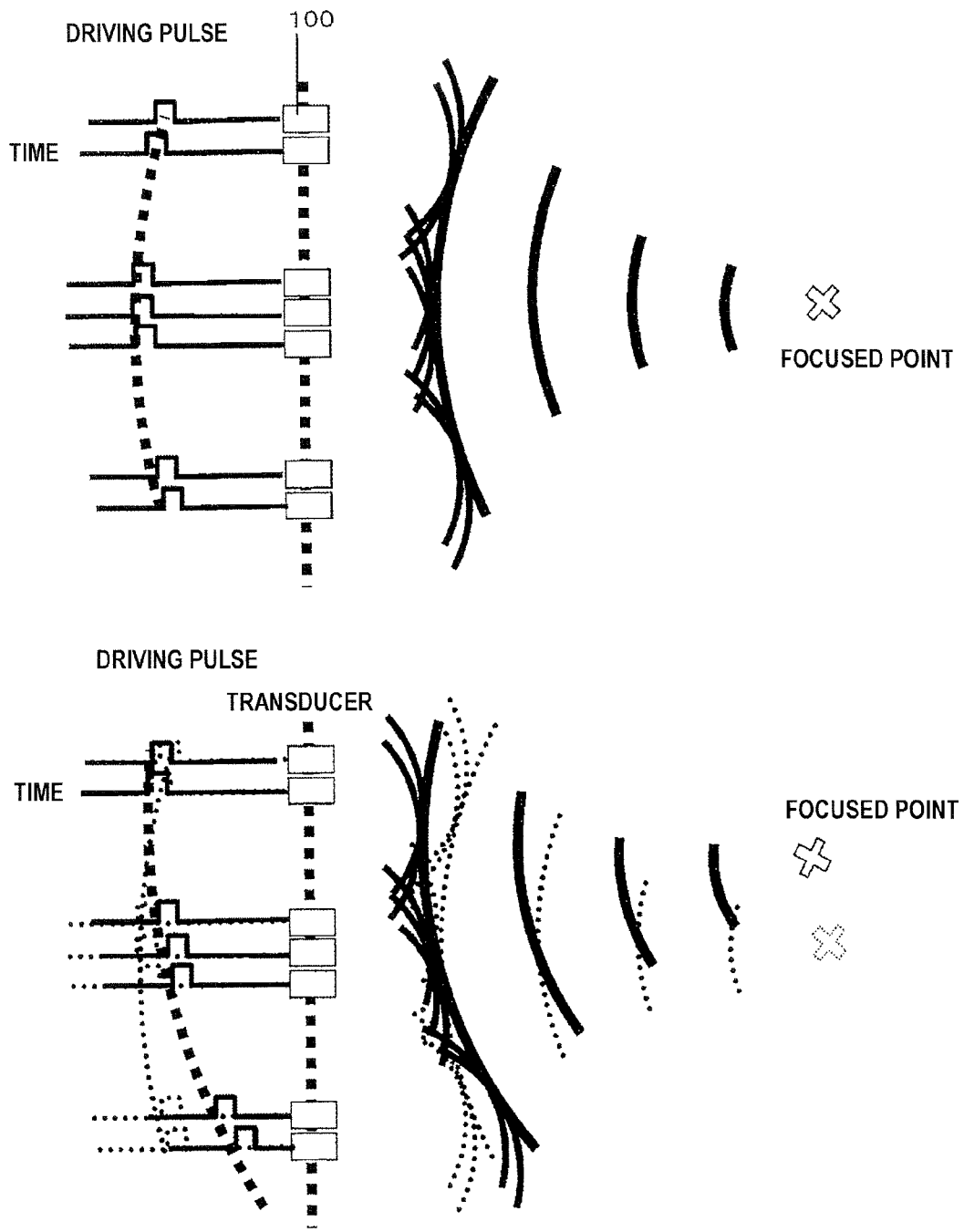
FIG. 3 illustrates beam forming of ultrasound waves by the ultrasound probe according to the first embodiment.

In the first embodiment, as shown in FIG. 2, an explanation will be made as to the case where a linear array type ultrasound probe 1 is used, being brought into contact with the body surface of a test object, and the ultrasound beam for displacement generation (hereinafter, also described as a focused beam) is focused onto two focused points. The two focused points are respectively positioned on two different rasters (scanning lines) on a target cross-sectional surface within the body, and they are located at the same depth from the body surface. As shown in FIG. 3, a distance between each of the focused points and each device 100 of the ultrasound probe 1 is obtained, and a difference of the distance with respect to each device is divided by a sound velocity of the target object so as to calculate a delay time, and the generator of transmit beam for displacement generation 13 performs transmission of the transmit signal that is provided with the delay time, thereby achieving the beam forming of the ultrasound beam that is focused onto the focused point.

Figure 4:
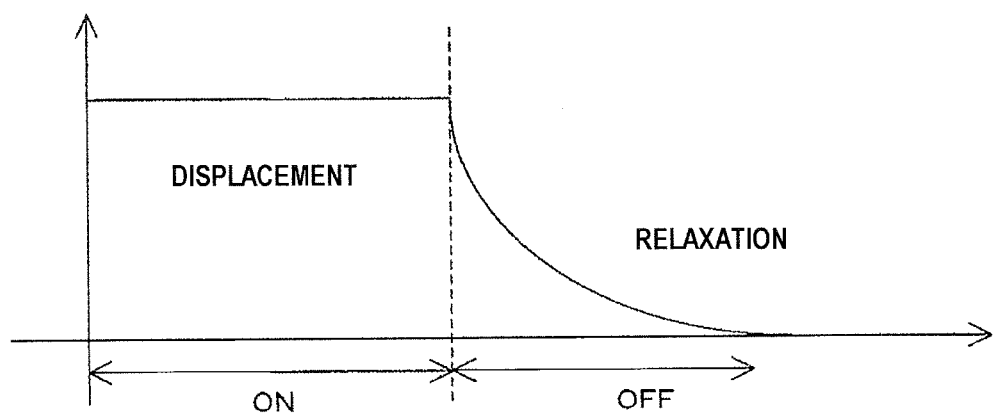
FIG. 4 is a graph showing a change of displacement and relaxation over time, occurring in the tissue of a test object, caused by a focused beam according to the first embodiment.

When the focused point is exposed to the focused beam, a radiation pressure is generated according to absorption or scattering of the ultrasound waves along with propagation. Under normal conditions, the radiation pressure becomes maximum at the focused point, generating displacement in the tissue of the living body within the region of the focused point, in the direction vertical to the body surface of the test object. On the other hand, when the exposure of the focused beam stops, the amount of displacement is relaxed (FIG. 4). Generation of the radiation pressure produces a shear wave and allows the shear wave to propagate in the direction parallel to the body surface of the test object, from each focused point as a starting point (FIG. 2).

Next, an explanation will be made as to a method for transmitting a focused beam according to a burst-chirp method suggested by the present invention. In the first embodiment, as shown in FIG. 2, the focused point F1 and the focused point F2 in the tissue of the test object are alternately exposed to the focused beam from one ultrasound probe 1, thereby generating displacement at the focused points F1 and F2 alternately. The time setter for beam 14 configures settings of switching timing between ON and OFF for exposing each focused point to the focused beam, and the CPU (Central Processing Unit) 3 controls starting and ending of the exposure on the two focused points.

Figure 5:
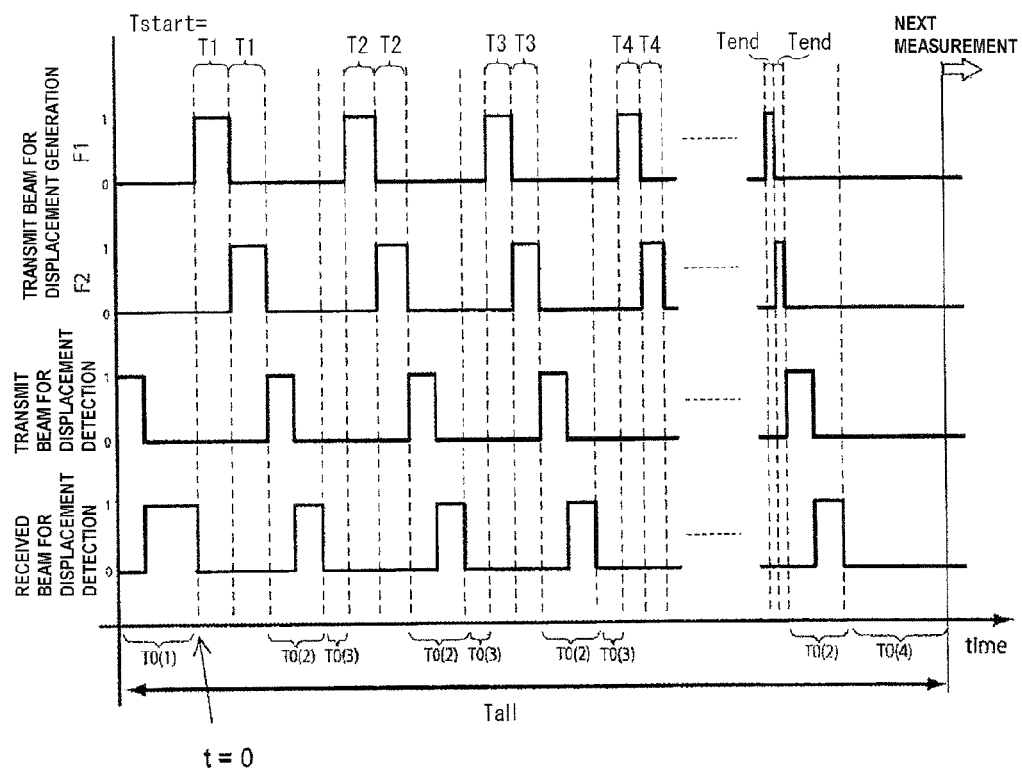
FIG. 5 is a diagram for explaining a sequence of the method of measurement according to the first embodiment.

With reference to FIG. 5, an explanation will be made as to the switching timing of the focused beam exposure, when the focused points F1 and F2 are alternately exposed to the focused beam. In the first embodiment, as shown in FIG. 5, while the focused point F1 and the focused point F2 of the test object tissue are alternately exposed to the focused beam in a repeated manner, the exposure time duration when one focused point is exposed to the ultrasound beam is gradually reduced. In other words, the period of switching the ultrasound beam exposure from the focused point F1 to the focused point F2 (T1, T2, T3, ... Tm, ... $T_{end}$; here, "m" represents the number of exposure cycles) is gradually reduced (sweeps), as the number of exposure cycles m becomes larger. In practice, the focused positions of the electric signals (transmit signals) which are transferred to the probe 1, are switched according to the switching period Tm (hereinafter, it is referred to as "burst-chirp method"). FIG. 5 shows a sequence of the transmit beam for displacement generation, when the interval between the switching periods Tm and T(m+1), i.e., ΔTm (=T(m+1)−Tm)) is a negative constant.

It is to be noted that in FIG. 5, the transmit beam for displacement generation indicates ON and OFF timing of the electric signal that the generator of transmit beam for displacement generation 13 transfers to the ultrasound probe, and the transmit beam for displacement detection indicates ON and OFF timing of the electric signal that the generator of transmit beam for displacement detection 22 transfers to the ultrasound probe 1. The received beam for displacement detection indicates ON and OFF timing of the electric signal that the operator of received beam for displacement detection 23 receives from the ultrasound probe 1. According to the operation of the time setter for beam 14 and the transmit-receive switch 2, at the timing indicated in the sequence shown in FIG. 5, the transmit beam for displacement generation is transferred to the ultrasound probe 1 for transmitting the focused beam alternately to the focused point F1 and the focused point F2, and the transmit beam for displacement detection is transferred to the ultrasound probe 1 for transmitting an ultrasound beam for detection which detects the displacement at a predetermined position. The operator of received beam for displacement detection 23 receives an echo signal that is reflected inside the test object and returns to the ultrasound probe 1, at the ON and Off timing of the received beam for displacement detection in FIG. 5. In practice, an operation for switching the received beam for displacement detection to the ON state, corresponds to the operation in the transmit-receive switch 2, i.e., disconnecting the generator of transmit beam for displacement detection 22 from the ultrasound probe 1, establishing connection between the operator of received beam for displacement detection 23 and the ultrasound probe 1, acquiring a receive signal, and carrying out the operation for performing the phasing and adding for the beam forming.

With reference to FIG. 5, a further detailed explanation will be made as to a method for transmitting a focused beam according to the burst-chirp method. The clock time of the first exposure of the focused beam is assumed as t=0. The transmit-receive switch 2 connects the generator of transmit beam for displacement generation 13 with the probe 1 at t=0, transfers a transmit beam for displacement generation (electric signal) to the probe 1, switches the focused beam exposure on the focused point F1 to the ON state (=1), thereby generating displacement at the focused point F1. On this occasion, the exposure of the focused beam on the focused point F2 is in the state of OFF (=0). Accordingly, a shear wave propagates from the focused point F1. During this period, the focused beam directed to the focused point F1 constantly stays in the state of ON, when the clock time t is in the range of 0≤t≤T1. Next, at the clock time t=T1, according to the operations of the time setter for beam 14 and the focused position setter 12, the waveform of the transmit beam for displacement generation is switched, and switching the focused beam for the focused point F1 to the OFF state, and simultaneously, the focused beam to the focused point F2 is switched to the ON state, thereby generating displacement at the focused point F2. Accordingly, a shear wave propagates from the focused point F2. Therefore, when the clock time t is in the range of T1≤t≤T1+T1, the focused beam directed to the focused point F1 is switched to the OFF state, and the focused beam directed to the focused point F2 is switched to the ON state. On this occasion, the switching period between the two focused points, from the focused point F1 to the focused point F2, is T1 (Tm, m=1).

When the exposure of the focused beam for the cycle of m=1 is finished, the transmit-receive switch 2 establishes connection between the generator of transmit beam for displacement detection 22 and the probe 1. The probe exposes a predetermined position to the focused beam for displacement detection. Next, the transmit-receive switch 2 disconnects the generator of transmit beam for displacement detection 22 from the ultrasound probe 1, and establishes connection between the operator of received beam for displacement detection 23 and the ultrasound probe 1. The operator of received beam for displacement detection 23 acquires a receive signal being an echo signal of the ultrasound signal from a predetermined position, and carries out an operation of phasing and adding for beam forming.

Next, exposure of the focused beam for the cycle of m=2 is carried out. The switching period of the focused beam (exposure time) T2 (Tm, m=2) is made shorter than T1 only by a predetermined time, and the focused beam exposure on the focused points F1 and F2, and detection of displacement are performed. Acoustic intensity of the burst signal (focused beam) to each focused point may be the same as that of T1, or it may be different therefrom. The operation above is repeatedly performed, while gradually reducing the exposure time (switching period) Tm, until it is repeated a predetermined number of cycles.

In accordance with the focused beam exposure, the shear waves produced respectively from the focused points F1 and F2, interfere with each other, cancel each other, and amplifying each other, along with propagation. On the other hand, heat is generated simultaneously with occurrence of displacement at each of the focused points.

Figure 6:
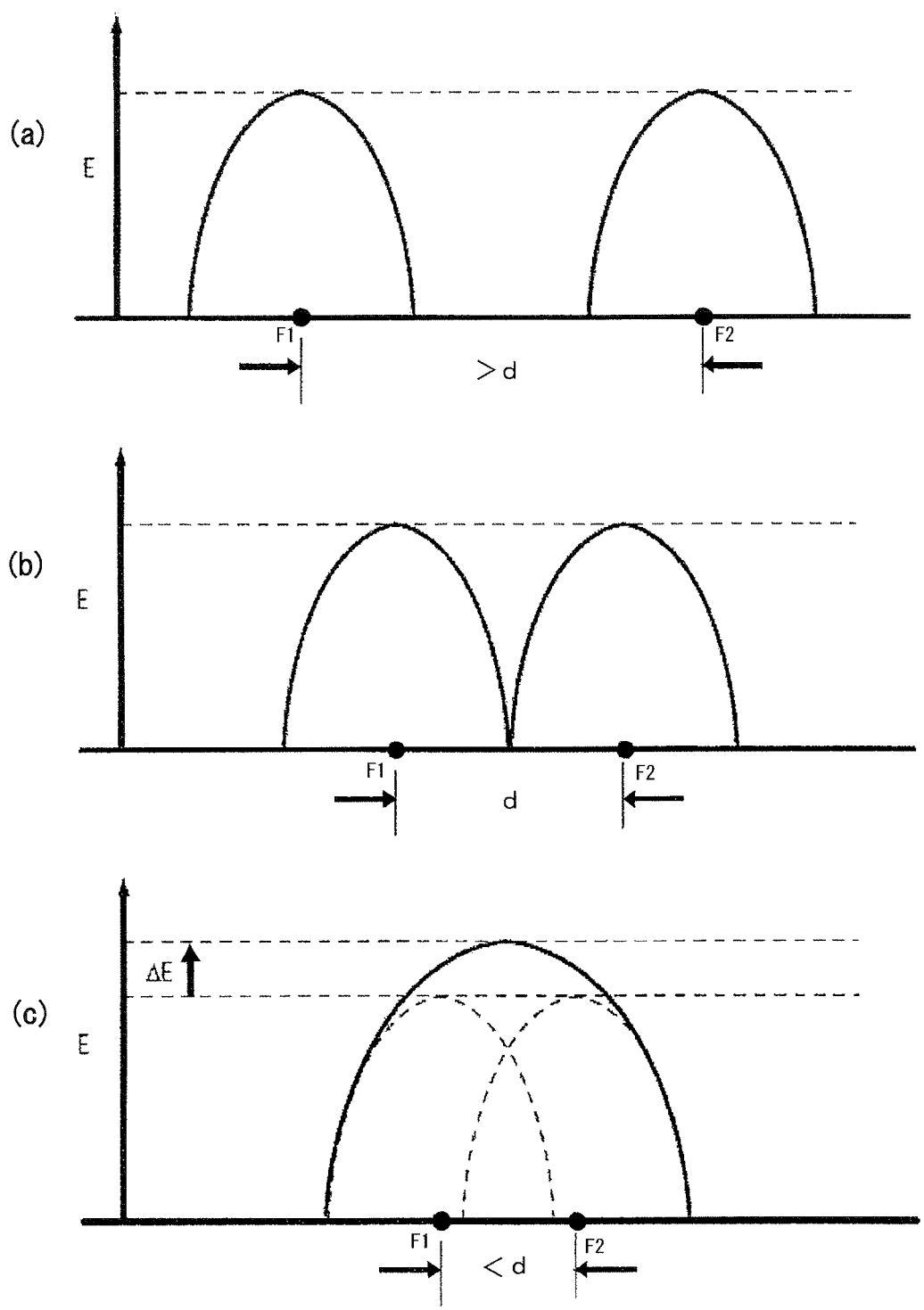
FIG. 6($a$), FIG. 6($b$), and FIG. 6($c$) illustrate a relationship between a distance of two focused points and a rise in temperature according to the first embodiment.

Next, a preferable range of distance between the two focused points will be explained. In FIG. 2, the distance between the two focused points is assumed as d. As the value of d becomes smaller, that is, the distance between the focused point F1 and the focused point F2 becomes narrower, a degree of interference between the shear waves becomes larger. However, when the distance between the focused points becomes narrower, there may be a rise in temperature E due to thermal conduction between the focused points, being possibly higher than the temperature at the focused points, and this may exert large influence on the tissue. Therefore, this is undesirable from the viewpoint of safety. On the other hand, if the value of d is made larger, the rise in temperature is diminished and the safety is improved, but a degree of interference becomes smaller, eventually. Therefore, an optimum value of d may be assumed as the value which ensures that a maximum value of the rise in temperature in the region between the two focused points is equivalent to the maximum value of the rise in temperature at each focused point, also the optimum value of d causing an interference between the shear waves. Specifically, the optimum value d is determined depending on the followings; such as a depth of the focused points, an exposure time duration of the focused beam, a frequency, and a site to be diagnosed (which may have an effect on the sound velocity of the living body, absorption of the ultrasound waves, thermal conductivity, and the like). Since the thermal conductivity of the living body is approximately 0.6 W/m/K, the range showing the rise in temperature in proximity to the focused point is approximately the same as the width of the focused beam, when the exposure time duration is around 1 ms. In order to make the maximum value of the rise in temperature in the region between the focused points to be equivalent to the maximum value of the rise in temperature at each focused point, the distance d is required to be equal to or more than the width of the focused beam. With reference to FIG. 6(a), (b), and (c), specific explanations will be made regarding the situation above. FIG. 6(a), (b), and (c) illustrate a relationship between the distance d and the rise in temperature E, in the case where the width of the focused beam is made approximately equal to a beam width of the focusing-type transducer, and the width of the focused beam is assumed as a diameter of a region (circle) where the energy density of the ultrasound waves at the focused position initially becomes zero. As seen from the waveform representing the rise in temperature at each focused point shown in FIG. 6(a), (b), and (c), the rise in temperature becomes maximum at the positions of the respective focused points F1 and F2, and it becomes zero at a distance more than the beam width d. Therefore, in the case where the distance d is more than the beam width as shown in FIG. 6(a) and in the case where the distance d becomes equal to the beam width as shown in FIG. 6(b), the maximum value of the rise in temperature at each focused point is equal to the maximum value of the overall rise in temperature that is obtained by adding each amount of rise in temperature one to another. On the other hand, as shown in FIG. 6(c), in the case where the distance d is less than the beam width, the maximum value of the total rise in temperature is increased by ΔE, from the maximum value of the rise in temperature at each focused position indicated by the dotted line. Therefore, it is found that safety regarding the rise in temperature can be maintained, under the condition that the distance d is made equal to or more than the beam width.

Here, an explanation will be made as to setting of an optimum value d when measurement is conducted. For the diagnosis of a liver, by way of example, the beam width is 1.8 mm, under the conditions that the focus depth is 4 cm, F-number is 1, and a carrier frequency is 2 MHz. Here, the F-number is obtained by the following calculation; focus depth/aperture size, and the beam width is obtained by the following calculation; (2.44*F-number*a wavelength of the carrier signal). A wavelength λ of the shear wave is approximately 0.2 mm, under the conditions that the beam exposure time, i.e., an average value of the switching period Tm is 180 μs, and the shear wave velocity is 1 m/s. In addition, with the carrier frequency as set above, a maximum value of propagation distance of the shear wave that is detectable by the experimental data is approximately 6 mm. According to those values described above, the value of d is set by using the beam width, the maximum propagation distance, and the wavelength λ of the shear wave, in such a manner that the distance d falls into the range, 10λ<d<30λ. Similarly, for the diagnosis of a breast, the beam width is calculated as 0.5 mm, under the conditions that the focus depth is 2 cm, the F-number is 1, and the carrier frequency is 7 MHz. The wavelength λ of the shear wave is approximately 0.1 mm, under the conditions that the average value of the switching period is 110 μs, and the shear wave velocity is 1 m/s. In addition, with the carrier frequency as set above, the maximum value of propagation distance of the shear wave that is detectable by the experimental data is approximately 3 mm. Therefore, the value of d is set in such a manner that the distance d falls into the range, 5λ<d<30λ. The CPU (Central Processing Unit) 3 reads this value d from a memory not illustrated, and it is set in the focused position setter 12. Moreover, based on the value d being set and a value of the shear wave velocity being estimated, a value relating to the switching period is determined.

Figure 7:
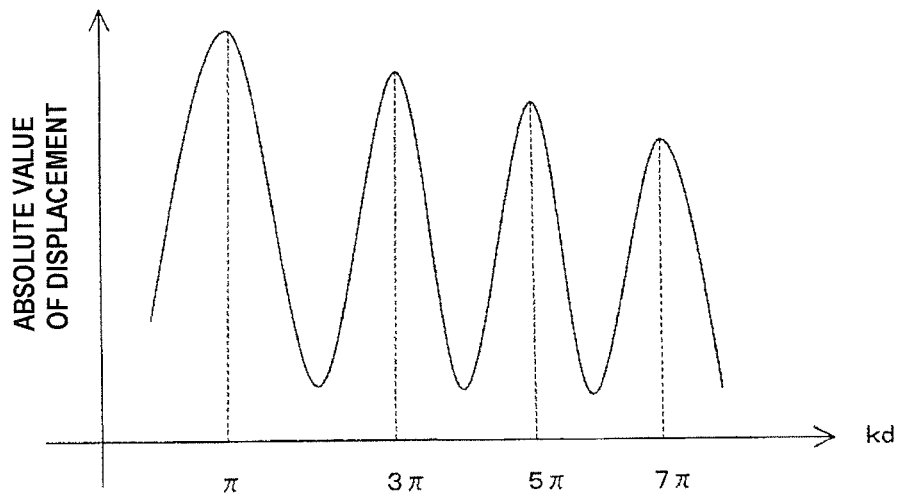
FIG. 7($a$) is a graph showing penetration of a shear wave generated by the method of measurement according to the first embodiment, FIG. 7($b$) is a graph showing a relationship between the displacement of the test object tissue and acoustic intensity, for the case where the two focused points are exposed to the focused beam, and for the case where one focused point is exposed to the focused beam, by the method of measurement according to the first embodiment.
Figure 7:
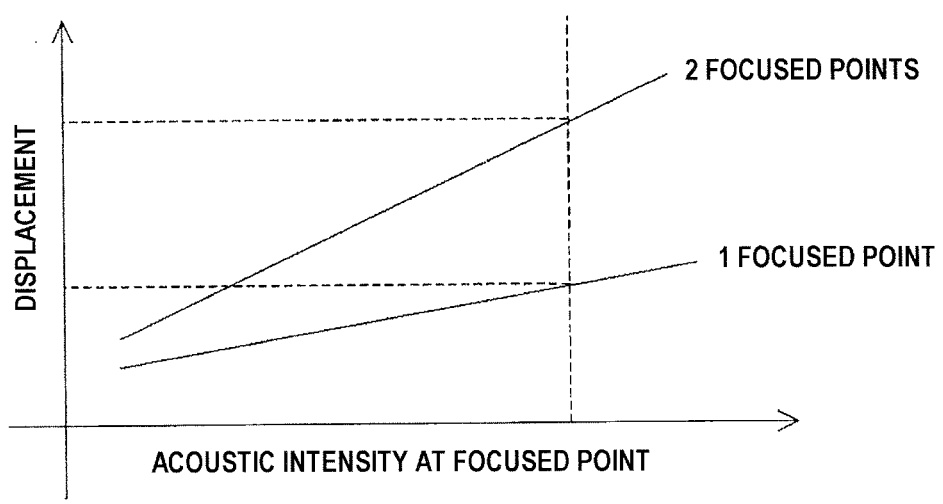

Next, an explanation will be made as to a method for calculating a value relating to the hardness in the calculator of hardness spectrum 26 in the displacement detector 20. In the present embodiment, the switching period Tm is changed, and when the shear waves produced from the two focused points F1 and F2 interfere with each other, causing an increase of the amplitude in a certain switching period, this switching period is obtained to conduct the measurement of the hardness. Hereinafter, an explanation will be made as to a condition under which the interference waves are amplified. The reciprocal of the switching period Tm is represented as a switching frequency (repetition frequency) fm, and it is defined as fm=1/Tm. Here, the condition where the interference waves are amplified and an absolute value of displacement becomes a peak value (maximum value) corresponds to the case where the distance d between the two focused points becomes (n+½) times more than the wavelength λ, and it is expressed by the following formula (1) (FIG. 7(a)). On this occasion, the switching frequency fm is represented as $f_M(n)$.

$$k*d=(2\pi f_M(n)/c)*d=2\pi(n+\tfrac{1}{2}) \qquad (1)$$

Here, k represents the number of waves (=2π/λ), c represents the shear wave velocity, and n represents 0 or a positive integer (n=0, 1, 2 . . . ). The shear wave velocity c is a value peculiar to a tissue property.

If a value of the switching period Tm when a peak value is obtained, is assumed as $T_M(n)$, satisfying $T_M(n)=1/f_M(n)$, and the following formula (2) is derived from the formula (1):

$$T_M(n)=d/c*(2/(2n+1)) \qquad (2)$$

By way of example, under the conditions that n=1 and d=2 [mm], if c=1 [m/s], $T_M(1)$=1.3 [ms] ($f_M(1)$=750 [Hz]), and if c=5 [m/s], $T_M(1)$=0.3 [ms] ($f_M(1)$=3.8 [kHz]).

As described above, the shear wave velocity c depends on the hardness of tissue, and as the tissue becomes harder, the value c becomes larger. Therefore, it is possible to estimate the hardness of the tissue based on the value of $T_M(n)$.

It is desirable to control the switching period Tm for switching the focused beam ON and OFF at the two focused points F1 and F2 within the range from a few Hz to several kHz.

The present invention features that the hardness is measured not by the period of a carrier signal of the focused beam, but by the switching period Tm between the two focused points F1 and F2, that is, the time control between ON and OFF. Therefore, by increasing the carrier frequency, imaging with a narrow beam width and a high spatial resolution can be performed.

Specifically, the calculator of hardness spectrum 26 subjects an output signal from the detector 25 to spectral analysis, then, obtains $f_M$ which makes the amplitude value to be the maximum, and $T_M$ associated therewith, and calculates a value relating to the hardness.

With the use of the technique of the present invention, as shown in FIG. 7(b), in the case where the acoustic intensity for each of the focused points is equal to the other, it is possible to obtain larger displacement by rendering the shear wave produced from the two focused points to interfere with each other, relative to the case where only one focused point is exposed to the focused beam.

Figure 8:
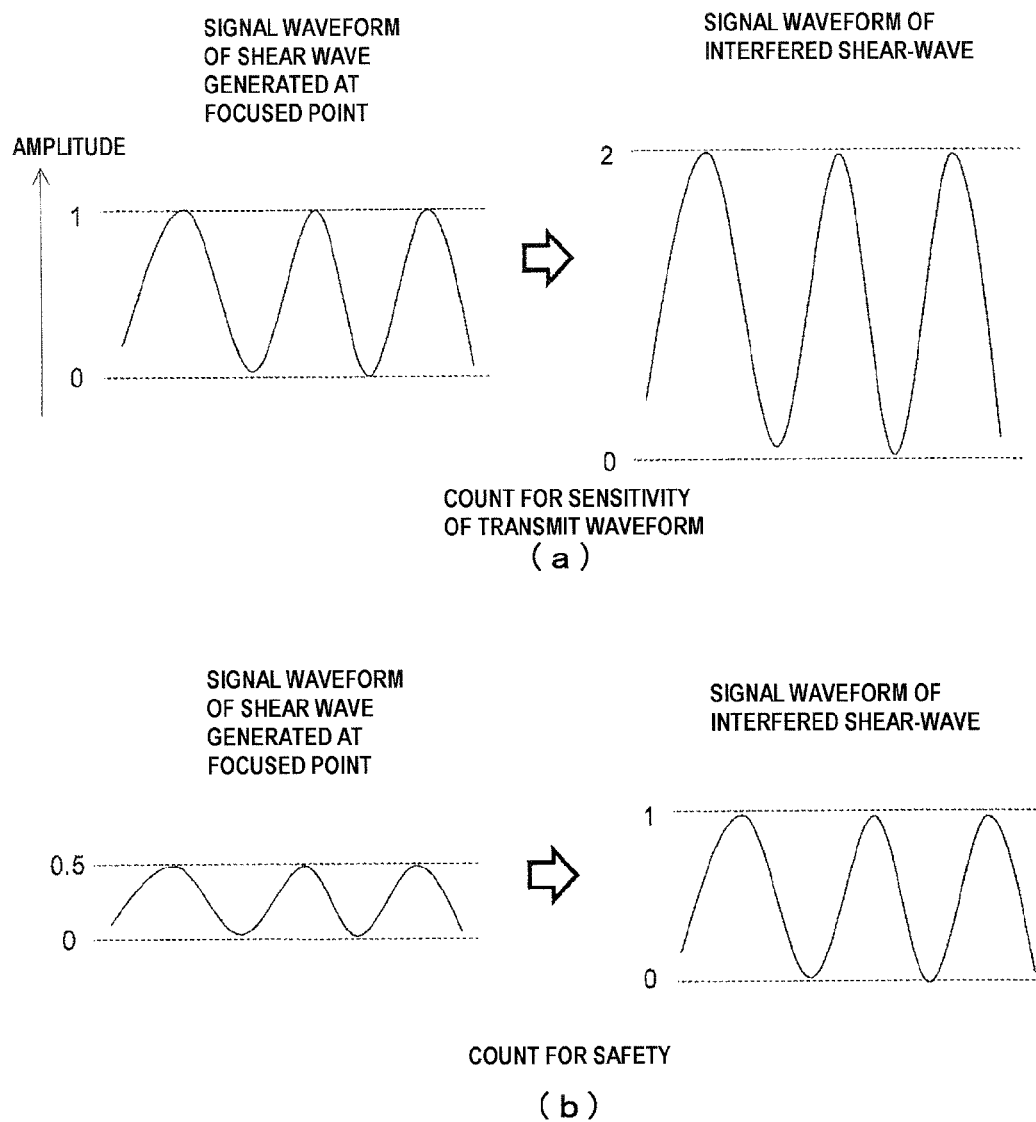
FIG. 8($a$) illustrates a waveform of the shear wave generated from each focused point and a waveform of the shear waves subjected to interference according to the technique of the first embodiment, placing importance on sensitivity of transmit wave, and FIG. 8($b$) illustrates the same, placing importance on safety.

FIG. 8(a) shows a signal waveform of the shear wave produced from one focused point, and an interferential waveform of the shear waves produced from two focused points. It is to be noted in FIG. 8(a), a minimum amplitude is assumed as 1, when one focused point is exposed to the focused beam and displacement of the shear wave is observable. By way of example, as shown in FIG. 8(a), if the amplitude of the shear wave produced by the focused beam directed to each of the focused points is 1, the amplitude of the interference wave becomes larger than that of before interference (ideally, two times larger), when the switching period becomes $T_M$. Therefore, it is possible to increase productive efficiency of displacement with respect to the transmit wave, in other words, heighten the transmit wave sensitivity. As shown in FIG. 8(b), if significance is placed on safety, the acoustic intensity of the focused beam directed to each of the focused points is made smaller. When the amplitude of the shear wave before interference is smaller than 1, the displacement of the shear wave is not measurable. However, in the case where the amplitude of the shear wave before interference is larger than 0.5, the amplitude of the interference wave at the time of the switching period $T_M$ becomes larger (ideally, two times larger), and the amplitude becomes equal to or larger than 1, thereby rendering the displacement to be detectable.

If the frequency and the form of the focused beam are the same, there is another method for improving the safety, in addition to the method as described above where the acoustic intensity is reduced by controlling the amplitude of the focused beam for displacement generation. This alternative method is to provide a time period to turn off the focused beam, for the time corresponding to the last n % of the period Tm (n: positive real number), within the period Tm during when the focused beam is supposed to be in the state of ON. It must be noted that in this case, the switching period Tm is kept unchanged even though the time being OFF is provided.

Figure 9:
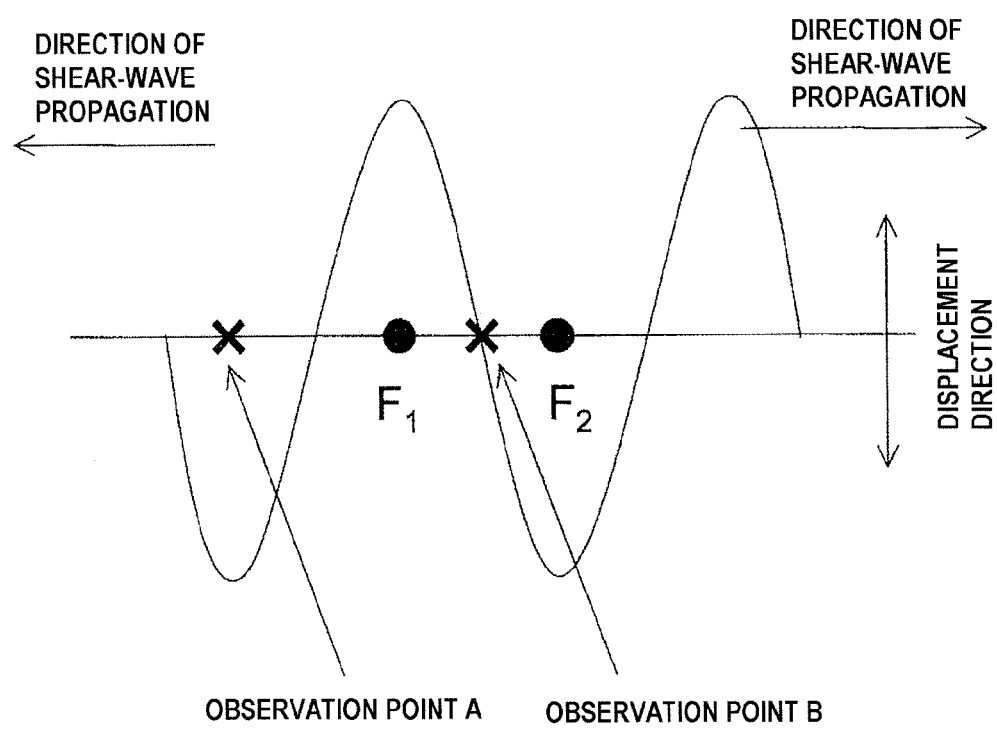
FIG. 9 illustrates a displacement direction in the test object tissue and a direction of shear-wave propagation according to the first embodiment.

In the method for measuring the hardness according to the present embodiment, the line segment connecting the two focused points F1 and F2 is not limited to being parallel to the body surface, and they may be at a slant with respect to the body surface. However, the generator of transmit beam for displacement detection 22 controls the received beam that is inputted into the operator of received beam for displacement detection 23, in such a manner that the direction of the received beam and the direction to which the shear wave proceeds are not parallel to each other, and preferably, they are orthogonal to each other to the extent possible. There is a reason for this. As shown in FIG. 9, the propagation direction of the shear wave is a direction orthogonal to the displacement direction, i.e., the direction of the focused beam for displacement generation. Therefore, if the propagation direction of the received wave beam and the propagation direction of the shear wave are parallel to each other, detection sensitivity for the displacement may disappear. Accordingly, setting of the line segment connecting the two focused points F1 and F2 is configured, preferably, in such a manner as parallel to the body surface, preventing that it is perpendicular to (placed on the same raster of) the body surface.

A displacement detection point which is exposed to an ultrasound beam is set at the position like the point A as shown in FIG. 9, and it is necessary to contrive the setting not to take a position like the point B as much as possible, where the displacement is minimum. This kind of contrivance is not so significant if the propagation of the shear wave is observed just as a transient phenomenon, for example, in a situation where exposure is performed on one focused point only. However, as in the present embodiment, when the two focused points are exposed to the focused beam, and displacement is detected, which is generated by the interference between the shear waves using the two focused points as sound sources, a local maximum point and a local minimum point of the absolute value of displacement (=amplitude value) are alternately distributed. Therefore, it is desirable to arrange some contrivance such as selecting a position where the absolute value of the displacement becomes the local maximum as the raster for monitoring the displacement, or setting multiple monitoring points to include the local maximum point as the observation point. In the case where multipoint monitoring is performed, it is possible to assume as an amount of displacement, a difference between the absolute value of the displacement at the local maximum point and the absolute value of the displacement at the local minimum point.

Figure 10:
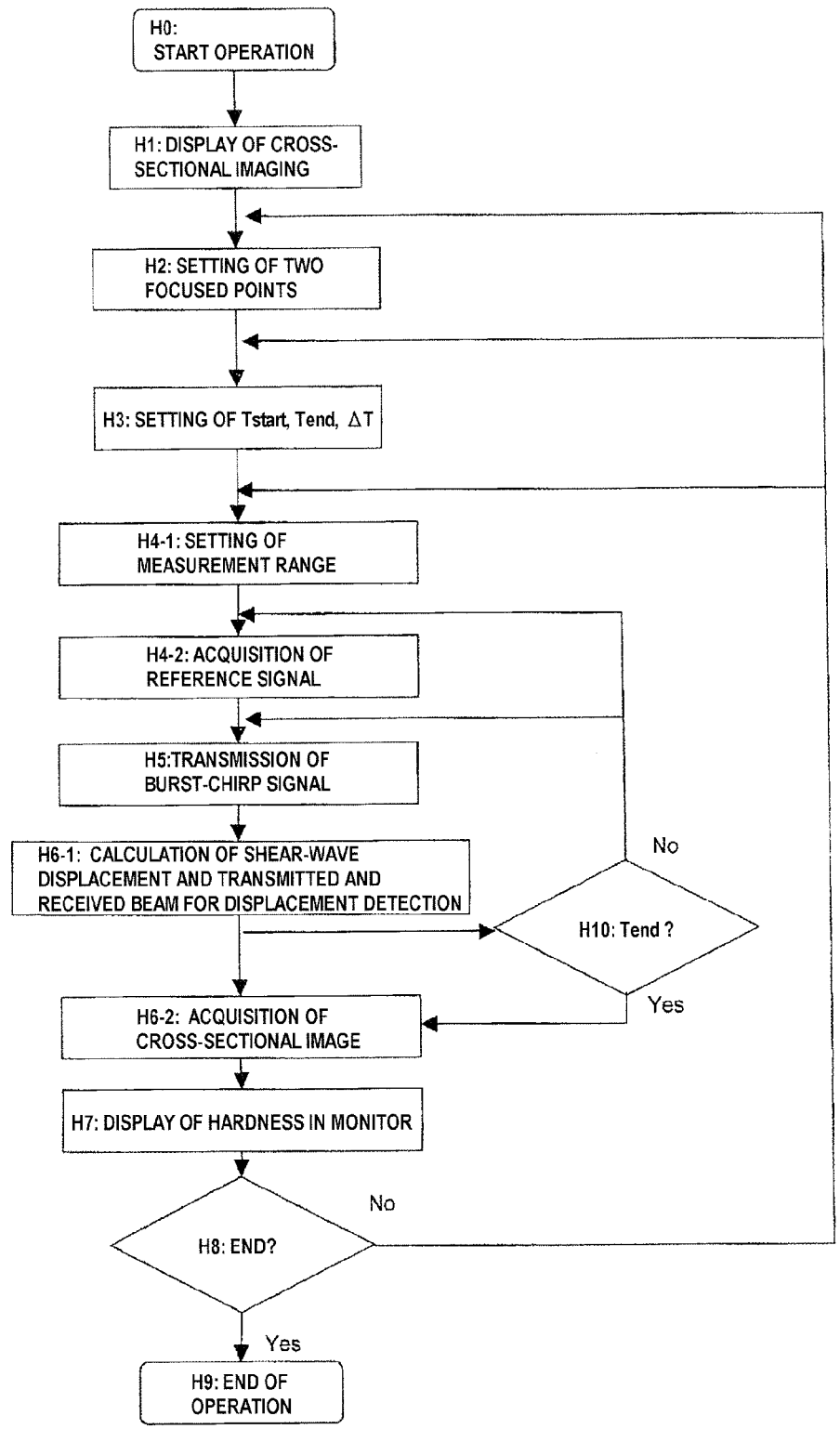
FIG. 10 is a flowchart showing a method of hardness measurement according to the first embodiment.

FIG. 10 is a flowchart showing the hardness diagnosing method of the ultrasonic diagnostic device according to the present embodiment. The measurement method includes a method for conducting measurement regarding one pair of focused points, and a method for conducting measurement along with scanning multiple pairs of focused points within a certain region in a cross-sectional plane.

Firstly, an explanation will be made as to the method for conducting measurement as to one pair of focused points. The operation starts in the step H0. In the step H1, firstly, there is displayed an image being taken in advance by transmitting and receiving an ultrasound wave for displacement detection. Here, it is assumed that the image being displayed is a B-mode image, or an elastography image that is taken according to a conventional method.

Next, in the step H2, the two focused points F1 and F2 are set. For these two focused points, the center point (here, indicating the center point of the line connecting the two focused points of each pair) between the two focused points is set as POI (Point of Interest), and the distance d between the two focused points is set. An operator may set the POI with checking the image displayed in the step H1, by using an input unit not illustrated (a keyboard, a mouse, a touch panel, or the like). Alternatively, it is possible to configure such that an estimate value is automatically set in the focused position setter 12, the estimate value being calculated based on a brightness value, the form of tissue, and the like, of the taken image. If the two focused points are automatically set, the step H1 may be skipped. If the operator configures the setting manually, it is possible to set the focused points, avoiding blood vessels and the like. Here, it is assumed that, as described above, the value of the distance between the two focused points is less than the distance which allows two shear wave to interfere with each other, and it is more than the width of the focused beam to which each focused point is exposed. In the case where the operator determines the focused positions, the aforementioned optimum value of the distance d (or a maximum value and a minimum value of the optimum distance d) is displayed in monitor, and the position is determined based on the value. When the distance d is set, according to an expected shear wave velocity, a value of n in the formula (2) and an optimum observation points are determined. Here, the observation point is determined based on the local maximum point of the absolute value of displacement in the shear wave, or based on multiple positions including the local maximum point, in the shear wave propagation distance. It is also possible to display the determined n and the observation point in the monitor.

Next, in the step H3, following values are set; an initial value $T_{start}$, an end value $T_{end}$, and an interval $\Delta T$, of the switching period Tm for time duration of the focused beam exposure, switched between the two focused points F1 and F2. The values set as the initial value $T_{start}$ and the end value $T_{end}$ are values which allow acquisition of a peak within the range satisfying the formula (2), with regard to the measurement site and the distance d between the two focused points. Those values may be automatically set according to the measurement site, a measurement depth, the distance between the focused points, and the like, or the operator may set those values via the input unit. Conversely, it is further possible to determine the value of n or the observation point in advance, followed by decision of the distance d. It is to be noted here that the distance d is a value within the range as describe above. In this case, the order is reversed between the step H3 and the step H2.

In the step H4-1, the measurement range is set. Firstly, the observation point (displacement detection point) of the shear wave is set. The observation point may be automatically set, or manually set by the operator via the input unit. In addition, a raster and sampling points on the raster are determined, which are used for detecting the amplitude (a few micrometers to several tens of micrometers) of the shear wave on the observation point. At each raster, a PRF (pulse repetition frequency: frequency of pulse repeatedly transmitted) for receiving the beam for displacement detection is set in such a manner as satisfying the Nyquist theorem, with respect to an expected shear wave frequency. For example, in the case where the direction of the raster is the same as the direction of the displacement of the shear wave, the PRF is set to be twice or higher than the shear wave frequency.

Next, in the step H4-2, a reference signal is acquired, which is used in a correlation operation (that will be performed in detecting displacement of the shear wave in the following). The reference signal is acquired by transmitting and receiving a beam for displacement detection to and from the raster within the measurement range, in the same manner as the step H6-1 described below. Alternatively, signal data of the B-mode image displayed in the step H1 may be used to acquire the reference signal. In this case, it is possible to skip the process of the step H4-2.

In the step H5, a burst-chirp signal (focused beam) is transmitted alternately to the two focused points F1 and F2, in the switching period of $T1=T_{start}$, and shear waves are produced respectively from the two focused points.

In the step H6-1, transmitting and receiving of the beam for displacement detection are carried out for observing the shear waves within the measurement range set in the step H4-1. Detection of the displacement at each measurement point may be constantly performed from the time when the burst-chirp signal is switched to the OFF state, until the shear wave arrives at all the observation points and passes therethrough. It is alternatively possible to configure such that the time from the arrival of the shear wave until the passage-through thereof is obtained in advance, based on the distance between the focused point and the observation point, and an estimated shear wave velocity, and the detection is conducted only for the obtained period of time. The latter case allows the PRF to be set higher, enabling highly precise detection of the displacement. The detector 25 extracts from the received signal, a signal corresponding to fm according to signal processing such as bandpass filtering, and thereafter, performs the already known correlation operation to calculate the displacement of the shear wave. The correlation operation is performed, by using the reference signal and an echo signal for each time being received from the beam for displacement detection. According to this calculation, it is possible to obtain a temporal waveform of the shear wave amplitude at each observation point.

In the step H10, it is determined whether or not the last switching period Tm is $T_{end}$. If it is not $T_{end}$, the process returns to the step H4-2 or to the step H5, again, and a burst-chirp signal is transmitted in the next switching period Tm+1. In the case where the process returns to the step H4-2, a reference signal is acquired again, and therefore, robustness is large in the correlation operation, due to a shift of the focused position during the measurement. In the case where the process returns to the step H5, after the move of the two focused positions, the measurement time can be reduced.

If the switching period is $T_{end}$, a B-mode image or an elastography according to the conventional method is taken in the process of the step H6-2. The sequence shown in FIG. 5 does not illustrate this image taking. If the image displayed in the step H1 is used, the process of the step H6-2 may be skipped.

In the step H7, spectral analysis is conducted based on the relationship between the absolute value of displacement and various switching periods (or switching frequencies), to calculate a value relating to the hardness based on the frequency $f_M$ and the period $T_M$ showing a peak, and the result of the calculation is displayed in the monitor. It is to be noted that when multiple observation points (displacement detection points) are set, a temporal waveform at the observation point as the following is used for the spectral analysis; i.e., the observation point with the largest value showing the absolute value peak of displacement of the shear wave.

Figure 11:
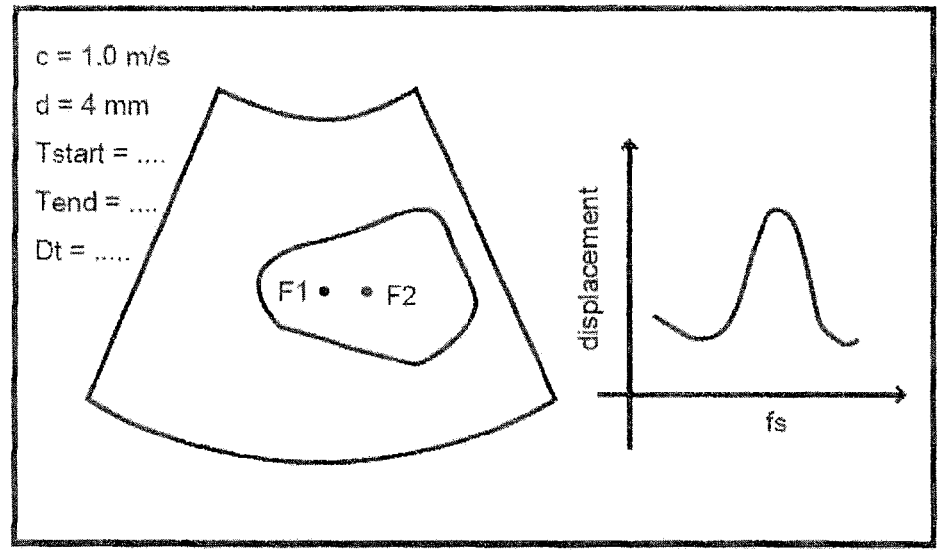
FIG. 11($a$) and FIG. 11($b$) illustrate a method for displaying a result of hardness measurement according to the first embodiment.
Figure 11:
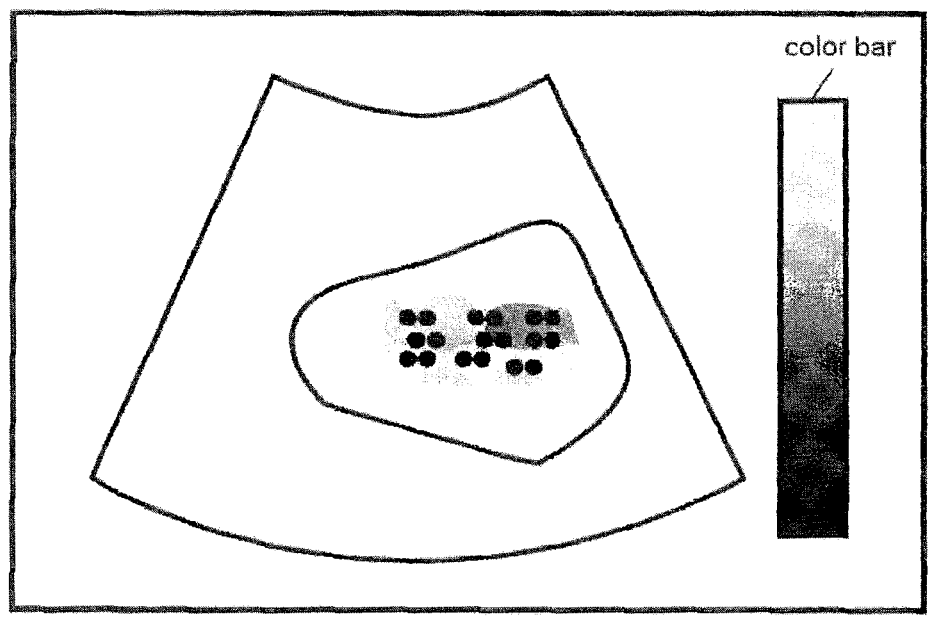

A result of the calculation is displayed in the form of numerical values, in the monitor together with the B-mode image or the elastography image according to the conventional method, taken in the step H1 or in the H6-2. The shear wave velocity c associated with $T_M$, the shear elastic modulus or the Young's modulus calculated from the shear wave velocity, and the like, are used as the values representing the hardness to be displayed. It is further possible to prepare a graph assigning Tm or fm as a horizontal axis, and assigning as a vertical axis, an amount of displacement, an amount of distortion, a brightness value, or the like, and display the graph in the same monitor as the B-mode image or the already existing elastography image, in such a manner as dividing the screen into two screens, or display them in switching manner. Furthermore, as shown in FIG. 11(a), the two focused positions F1 and F2, and the distance d may be displayed in such a manner as superimposing on the image, or they may be displayed together with the initial value $T_{start}$, the end value $T_{end}$, and the interval $\Delta T$ of the switching period for the time duration of the focused beam exposure, within the monitor. With the configuration as described above, the operator is allowed to change measurement parameters such as the two focused positions, the distance d, the initial value $T_{start}$, the end value $T_{end}$, and the interval $\Delta T$ of the switching period, with reference to the image and graph being displayed, and then conduct remeasurement.

In the step H8, the operator determined whether or not the measurement is terminated. If the two focused positions, and the values of the initial value $T_{start}$, the end value $T_{end}$, and the interval $\Delta T$ of the switching period, and a value relating to the measurement range are reset for measurement, the procedure returns to the step H2, the step H3, or the step H4-1 and the diagnosis is carried out again. If the remeasurement is not conducted, the measurement is terminated in the step H9.

Here, in the case where the test object moves in the course of measurement while Tm being changed, a method for correcting the moved focused positions will be explained. Upon returning from the step H10 to the step H4-2 and acquiring a reference signal, two-dimensional data including the focused positions set in the step H2 and estimated moved positions of the focused positions are acquired by transmitting and receiving ultrasound waves, and a vector of the moved distance of the focused points is calculated according to a well known vector matching method, by using the data within the corresponding range in the B-mode image data displayed in the step H1, and the two dimensional data previously acquired in the step H-2. The positions of the present two focused points are calculated based on the vector representing the moved distance being obtained, and the calculated positions are superimposed on the B-mode image acquired in the step H1, to display loci of the two focused positions, thereby allowing the operator to observe the test object's motion. It is further possible that in the step of H-2, all the data in the frame is acquired, and the moved distance may be calculated by using the data within a corresponding range, out of all the data. On this occasion, the B-mode image of the frame may be updated, together with displaying the loci of the positions.

The reference signal is also corrected in conformity to the moved two focused positions. The calculation of the moved distance may be performed every time after detecting the displacement for each switching period Tm, or the calculation may be performed after multiple number of periods Tm. In the step H4-2, in the case where the calculation is performed every time after detecting the displacement, the robustness for the motion becomes high. On the other hand, in the case where the moved distance is calculated after detecting the displacement for multiple periods Tm, the measurement time is made shorter, and therefore, it is effective if there is not so much motion. In addition to displaying the loci of the focused positions in the step of H4-2, when the hardness is displayed in the step H7, the locus of the moved distance, the focused positions set in the step H2 together with the final focused positions, vectors between the focused positions set in the step H2 and the final focused positions, and the like, may also be displayed. It is further possible to display following two results in the same monitor side by side; both the result of measurement without correcting the focused positions, and the result of the measurement to which the correction is applied. Alternatively, those results are displayed in a switched manner. The operator is allowed to check the followings; even though the position to be measured is moved, the hardness is not changed so much, or variation is found in the measurement results, and so on.

If the measurement is repeated multiple times for one pair of the focused points, numerical values of only the latest measurement result may be displayed, for instance. Alternatively, a result of each measurement is stored in a recording medium not illustrated, and numerical values of the multiple measurement results are listed, or displayed using a table, a graph, and the like. In addition, an average value and a variance of the multiple measurement results may be displayed. Values of the result of each measurement for the same two focused points or results of the measurement at spatially different two focused points, may be used to obtain the average value and the variance. In addition to displaying the result as numerical values, there is another method to display the result of measurements at multiple positions, in a two-dimensional manner, in the form of a grayscale brightness values or a color map. In this case, it may be displayed in the form of the color map superimposing on the B-mode image, displayed using two screens in the same monitor together with the B-mode image or the elastography image according to the conventional manner, or displayed in a switched manner. It is further possible to display a color bar. Furthermore, numerical values may be displayed therewith. The two-dimensional image being displayed may be a result of the latest measurement only, or alternatively, an average value of the multiple measurements may be displayed.

Next, an explanation will be made as to a method for setting multiple pairs of focused points in a certain region within a cross-sectional plane, and conducting measurement while scanning the positions of those pairs of the focused points. It is to be noted here that the explanation will be made with an emphasis on the part different from the aforementioned flowchart which shows the measurement without scanning.

In the step H2 of FIG. 10, multiple pairs of two focused points are set as an LOI (Line of Interest), or as an ROI (Region of Interest). The center point of the pair of the two focused points is set on a certain straight line for the case of the LOI. On the other hand, in the case of the ROI, it is set on a square or an outline shape of the measurement site, or the like. The operator may be allowed to input the LOI or the ROI via the input unit. It is further possible that the outline of the measurement site, and the like, are extracted from the cross-sectional image displayed in the step H1, according to image processing, and automatically set as the LOI or the ROI. After setting the LOI or ROI, a distance between the two focused points of each pair, the number of the pairs of the focused points, and a distance between the center points of multiple pairs of focused points, are set. It is to be noted, however, the distance between the two focused points is assumed as within the range as described above. In addition, the distance between the pairs of the focused points is set in such a manner that the shear waves propagating from each pair of focused points do not overlap one another. On this occasion, since the propagation distance of the shear wave>the beam width of focused beam, a rise in temperature at measurement time of each pair of focused points does not interfere with each other. When the operator performs the input, a settable distance between each pair of two focused points, the number of the pairs of the focused points, and a distance between the center points of multiple pairs of focused points are displayed. The center of each pair of the focused points may be arranged equally spaced, or not equally spaced.

In the step H4-1, the measurement range for each pair of focused points is set automatically or by the operator via the input unit. In addition, the order of measurement is set up for each pair of focused points. Upon setting the pair of two focused points, the pairs in the neighboring order, are selected from the positions as distant as possible (e.g., at the upper left position and the lower right position). This is meant to avoid impact on the living body due to a rise in temperature which is caused by the focused beam exposure at each pair of two focused points.

In the processes of the step H5 and the step H6-1, a burst-chirp signal of the switching period Tm is transmitted to each pair of the focused points and displacement is detected, in the order set in the step H4-1. When displaying operation is performed in the step H7, for example, a display as a color map is created, superimposing the color map on the B-mode image taken in the step H6-2, a two-screen display is created in the same monitor together with the B-mode image, or those images are displayed in a switching manner. It is further possible to display the color bar. In addition, the positions of the LOI, ROI, and the focused points may be displayed. The operator checks the following; there is not so much difference in the hardness depending on the positions to be measured, there are variations depending on the positions, or the like. With regard to the two-dimensional display showing the result relating to the hardness, it is possible to configure such that if the operator designates an arbitrary point in the ROI via the input unit, a value as to the hardness may be displayed in the monitor. It is additionally possible to calculate an average value and a variance of the measurement results as to multiple pairs of focused points and display those values in the monitor.

Here, similar to the case of one pair of focused points, there is a possibility that the positions of each pair of focused points may move in the cross-sectional plane, in the course of measurement. Therefore, in the same manner as the case of one pair of focused points, in the step H4-2 from the second time, an amount of vector indicating the movement of each pair of the focused points is calculated, allowing the reference signal to be updated. In the step H7, as shown in FIG. 11(b), according to the calculated vector amount indicating the movement, the positions of the focused points and a location for showing the hardness are corrected, and final positions of each pair of focused points may be displayed. Similar to the case of the measurement of one pair, as for the vector indicating moved distance, the loci of the focused points may be displayed in such a manner as superimposing on the B-mode image, being updated upon changing the switching period Tm.

Hereinafter, variations of the method for measuring the hardness according to the first embodiment will be described.

As shown in FIG. 7(a), if multiple peaks are observed in measuring the hardness of one pair of two focused points, the peak may be estimated from an average of multiple number of values c, calculated from multiple switching periods $T_M(n)$ by using the formula (2). It is alternatively possible to estimate the hardness from the interval $\Delta T_M = T_M(n+1) - T_M(n)$ of the switching period $T_M(n)$ showing a peak, or estimate the hardness from an average value of the interval of $\Delta T_M$ of multiple number of switching periods. Here, $\Delta T_M$ is derived from the formula (2), as the following formula (3):

$$\Delta T_M = d/c^*(-4/((2n+1)^*(2n+3))) \quad (3)$$

In the description above regarding the first embodiment, it is controlled in such a manner that the two focused points F1 and F2 are alternately exposed (ON/OFF) to the focused beam. It is further possible to control so that those points are simultaneously exposed (ON/OFF), and cause displacement at the same clock time on the two focused points F1 and F2. On this occasion, the condition under which the interference wave is amplified to have a peak value is that the distance d between the two focused points is (n+1) times longer than the shear wave wavelength λ, and therefore, following formula (4) is obtained in association with the formula (1):

$$k^*d = (2\pi f/c)^*d = 2\pi(n+1) \quad (4)$$

It is further possible to configure a high-precision method for measuring the hardness, as the following; for the first time, measurement is conducted with roughly setting the interval ΔT of the switching period, and $T_M$ is obtained. Then, in the next measurement, the ΔT is set in detail in the switching period near the $T_M$, to obtain more detailed $T_M$ value.

In the description above regarding the first embodiment, each of the two focused points F1 and F2 is exposed to one-time focused beam in each switching period Tm, and the period is changed to the next switching period T(m+1). However, the operation is not limited to this example. It is further possible that the focused points are alternately exposed to focused beam for multiple times in the same switching period Tm, and thereafter, the next switching period T(m+1) is set. Multiple exposures alternately repeated in the same Tm may enable a highly sensitive measurement.

In the aforementioned first embodiment, the value of the switching period Tm is changed from a large value to a small value, but conversely, it is further possible to change the value from a small value to a large value. In addition, ΔTm may be changed based on a certain function such as geometric series, other than a fixed value.

Further in the first embodiment, an explanation has been made as to a method for estimating the hardness from the peak value (local maximum value), but a local minimum value may also be applicable. In this case, in FIG. 7(a), values of kd=2π, 4π, . . . are used. It is further possible to estimate the hardness from the interval between the local maximum value and the local minimum value. The interval between the local maximum value and the local minimum value corresponds to a value obtained by multiplying by ½, the interval of the peak value $\Delta T_M$ expressed in the formula (3), and thus it is possible to reduce time, relative to the time for measuring the interval of the peak value.

In the first embodiment, the method for exposing the two focused points to the focused beam is explained. It is further possible that two or more (e.g., four) focused points are set equally spaced on one straight line within the living body, every other focused point is exposed to the focused beam in the same sequence as that of the focused point F1 or the focused point F2 (e.g., the sequences as shown in FIG. 5 are applied from the end of the four focused points in the following order; the sequence of the focused point F1, the sequence of the focused point F2, the sequence of the focused point F1, and the sequence of the focused point F2). With the configuration above, the number of waves interfering with each other is increased, thereby enhancing the sensitivity while further maintaining the safety.

Figure 12:
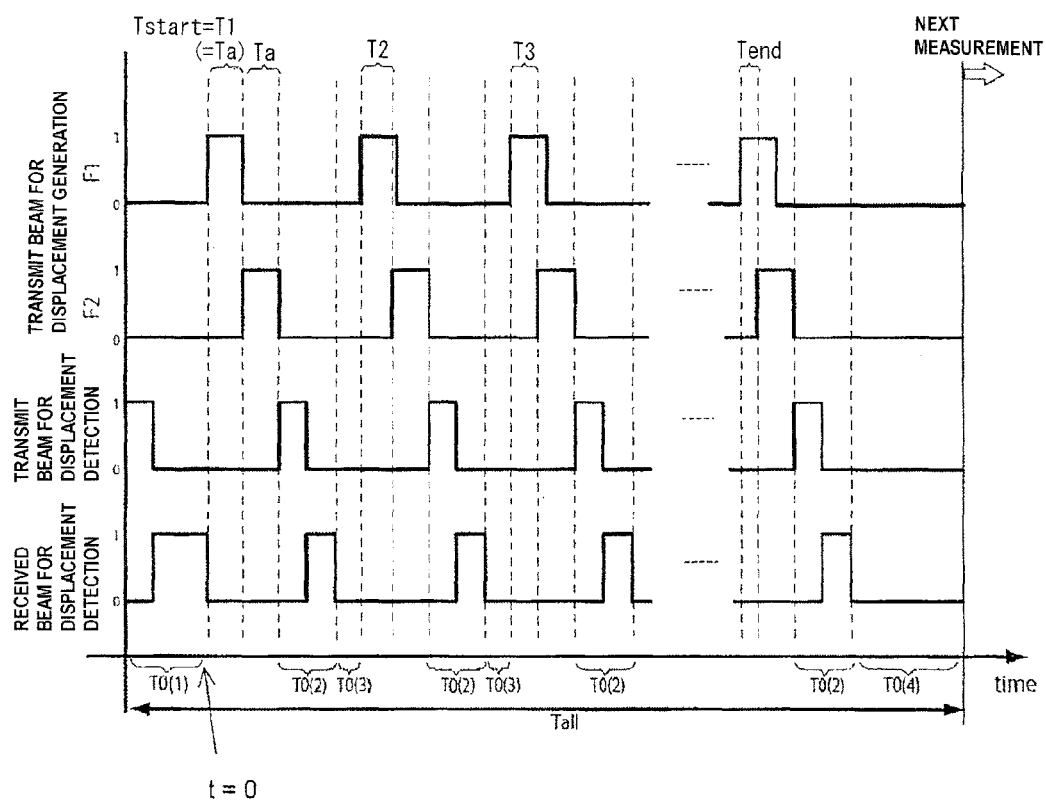
FIG. 12 illustrates a sequence of a method of measurement according to a second embodiment.

In the first embodiment, an ultrasound wave is transmitted and received while sweeping the switching frequency fm of the focused beam, being switched between ON and OFF. However, it is further possible to conduct measurement using only a particular switching frequency fm. By way of example, the measurement is conducted according to the method as shown in FIG. 12. In this case, more precise measurement is possible by conducting the measurement, with the settings of an optimum distance d between the focused points and a particular switching frequency, based on the shear wave velocity c that is obtained by the diagnosis of the hardness according to the burst-chirp method.

Another method is also conceivable in which the switching frequency fm is fixed, and measurement is conducted while changing the distance d between the focused points. In this method, the focused position of the focused beam is variable, thereby enabling more safe measurement.

Instead of switching the burst switching frequency fm in transmitting a beam, a random wave including multiple frequencies fm may be employed, thereby allowing the focused beam exposure and transmitting and receiving of the beam for displacement detection to be performed only once. Spectral analysis is carried out after calculating the displacement of the shear wave, and displacement for multiple frequencies fm is calculated. With this configuration, it is possible to reduce the measurement time.

A target for the measurement may be, for instance, a liver, a breast, a blood vessel, and the like.

Second Embodiment

In the second embodiment, the switching period of the time duration of beam exposure for exposing one focused point out of the two focused points is kept constant, and only the switching period of the time duration of beam exposure for exposing the other focused point is changed. In other words, this relates to a method for sweeping the phase.

With reference to FIG. 12, the second embodiment will be explained. As indicated by the sequence of the focused beam shown in FIG. 12, the time width of the focused beam when the focused point F1 is ON and the time width of the focused beam when the focused point F2 is ON are assumed as Ta (fixed). In addition, it is controlled so that a value of the time width Tm from the time when the focused beam directed to the focused point F1 becomes ON to the time when the focused beam directed to the focused point F2 becomes ON is made gradually smaller by a constant interval ΔT, such as from T1(=$T_{start}$=Ta), T2, T3, and so on. With the method, it is not necessary to change the setting of the value of the switching period for the focused point F1, and therefore, the measurement time can be reduced.

At each of the two focused points, the time width when the focused beam is ON is Ta in both, and therefore, the acoustic energy and the amount of displacement at the two focused points are the same.

Figure 13:
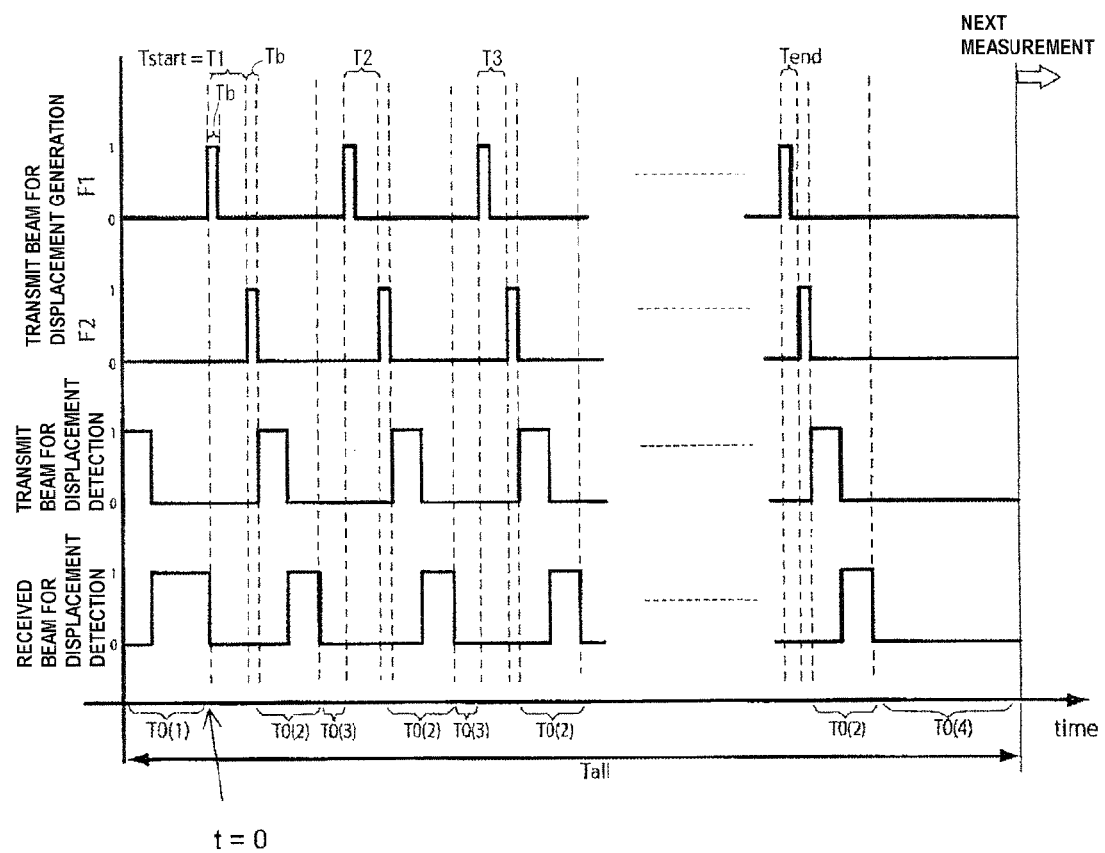
FIG. 13 illustrates a sequence of another method of measurement according to the second embodiment.

It is further possible that as shown in FIG. 13, the time width when the focused point F1 and the focused point F2 are ON (exposure time) is fixed to Tb, and the time width Tb is set to be sufficiently short, so that the time when both focused point F1 and the focused point F2 are ON do not overlap one another. On this occasion, since the two focused points can be separately exposed to divided focused beams, there is no influence of interference between the beams. The time Tm from the time when the focused beam directed to the focused point F1 becomes ON to the time when the focused beam directed to the focused point F2 becomes ON is made gradually smaller by a constant interval $\Delta T$ (Tm=T1 (=$T_{start}$), T2, T3, and so on). Another method for gradually increasing the value of Tm is also applicable. In the step H3 of the flowchart as shown in FIG. 10, the value of Ta or Tb is set, in addition to the initial value $T_{start}$, the end value $T_{end}$, and the interval $\Delta T$.

Third Embodiment

Figure 14:
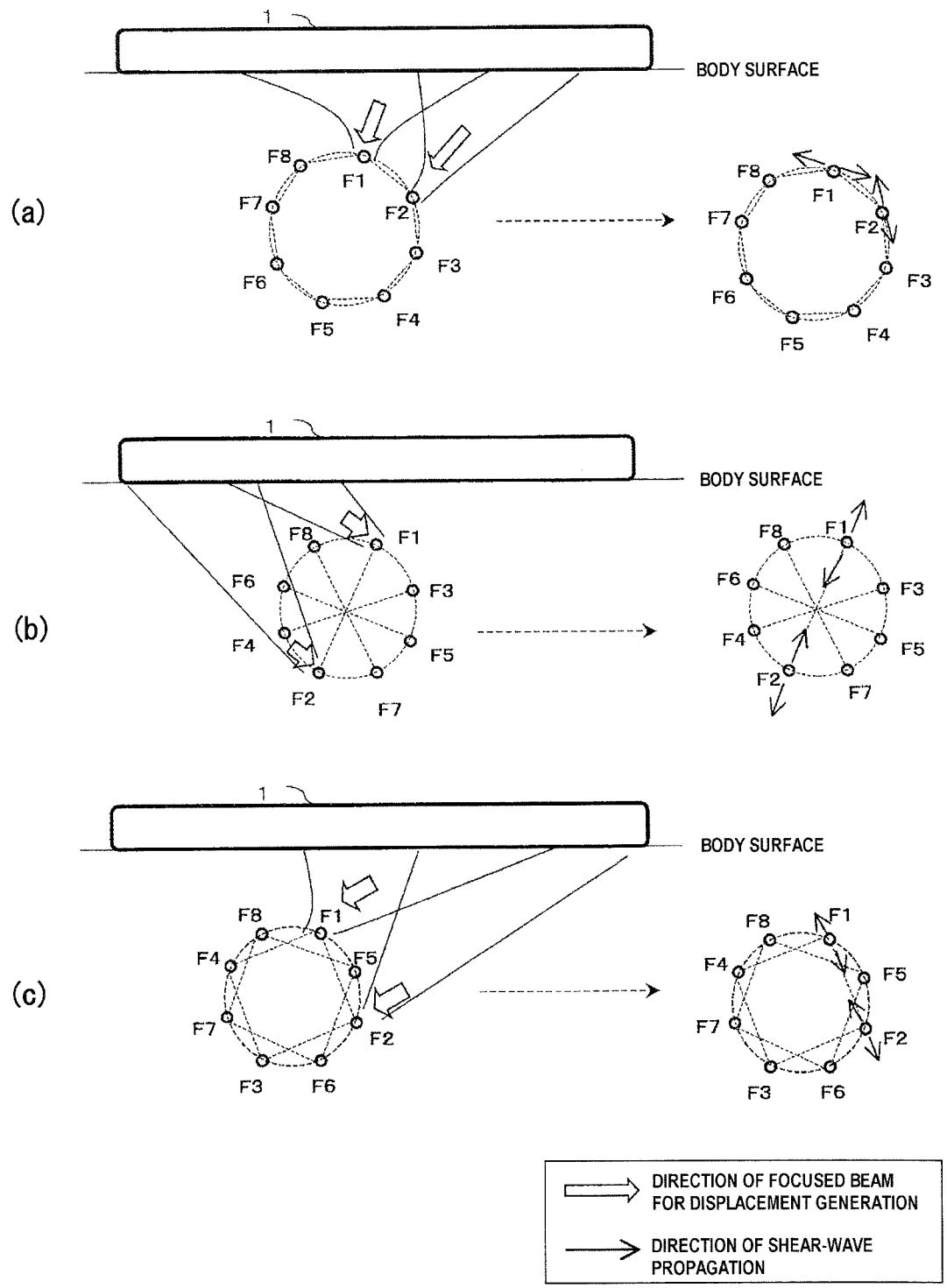
FIG. 14($a$), FIG. 14($b$), and FIG. 14($c$) illustrate a method for conducting measurement as to the eight focused points according to a third embodiment.

In the present embodiment, an explanation will be made as to the measurement that is conducted with focusing on multiple points, in order to diagnose the hardness on a measurement site two-dimensionally. FIG. 14 illustrates directions of the focused beam exposure when the measurement is conducted at eight focused points F1, F2, F3, F4, F5, F6, F7, and F8 on a concentric circle, and propagation directions of shear waves that are produced along with the exposure. In the present embodiment, the number of the focused points is set to be eight, but the number of the focused points is not limited to this number. FIG. 14(a), (b), and (c) illustrate variations of a pair of two focused points. By way of example, FIG. 14(a) illustrates that neighboring points, that is, the focused point F1 pairs with the focused point F2, the focused point F2 pairs with the focused point F3, the focused point F3 pairs with the focused point F4, and so on. Measurement of those pairs is particularly effective, in the case where the hardness of the outline of a tissue form needs to be measured. In FIG. 14(b), the focused point F1 and the focused point F2, the focused point F3 and the focused point F4, and the focused point F5 and the focused point F6 are respectively pairs of the two focused points opposed to each other. Such configuration is useful when measurement of the hardness inside the measurement site is required. The pairs being associated are not limited to those described above. As shown in FIG. 14(c), a focused point may pair with a focused point next but one, or other pairs may also be possible.

A method for displaying the result of each of the examples shown in FIG. 14(a), (b), and (c) may be a display of an average value or a variance value of the values indicating the hardness measured in the two pairs, or a two dimensional display using an intensity image or a color mapping may also be applicable. It is further possible to display an average value, a variance value, a two-dimensional display of the measured values, and the like, for two or more variations as shown in FIG. 14(a), (b), and (c). Here as described above, the line segment of each pair of two focused points is positioned in such a manner as not being in a direction vertical to the body surface, that is, not on the same raster of the ultrasound probe 1.

The measurement site and a combination making the pair may be determined by the operator via the input unit, or they are set on the places that are estimated from the image taken in advance. In the present embodiment, the focused points are set on a concentric circle, but the shape is not limited to this. Information of some shapes, for example, information regarding a circle and a quadrangle, is stored in a memory not illustrated, within the ultrasonic diagnostic device, and the operator may be allowed to freely move or deform the shape on the monitor to determine the combination of the pair described above. Alternatively, it may be any shape formed by inputting each point by the operator.

The order of the pairs of two focused points for transmitting and receiving ultrasound waves may be set in a clockwise manner, such as F1 and F2, F2 and F3, and F3 and F4 as shown in FIG. 14(a), or it may be set in a counterclockwise manner. It is alternatively possible to make pairs excluding next one, such as F1 and F2, F3 and F4, and F5 and F6. Also for the examples shown in FIG. 14(b) and FIG. 14(c), the measurement order of the pairs may be controlled.

The flowchart shown in FIG. 10 may be modified for the third embodiment, just by adding a process to repeat the step H5, the step H6-1, and the step H6-2, until completing measurement of all the pairs of two focused points. The pair of focused points may be automatically set, or set by the operator. If the operator configures the settings, the setting is performed in the step H2.

Next, an explanation will be made as to the variations of the third embodiment.

In order to improve the frame rate, if the pairs such as the focused point F1 and the focused point F2, the focused point F5 and the focused point F6, have line segments connecting the two focused points, being orthogonal to each other, the propagation direction of shear waves are different by 90 degrees. Therefore, it is possible to combine a burst-chirp sequence of one pair, into a burst-chirp sequence of another pair, like the sequence shown in FIG. 15. By way of example, here it is assumed that the switching period for the focused beam directed to the focused point F1 and the focused point F2 is T1, T2, T3, . . . and Tm. On this occasion, the switching period for the focused beam directed to focused point F5 and the focused point F6 is assumed as S1, S2, S3, . . . and Sm (Sm=n*Tm, n is a positive real number). Here, it is assumed that Tm is not equal to Sm. As described above, if the switching periods for the respective pairs are different, the frequencies of the shear waves generated therefrom are also different. If the bandwidths of both switching frequencies do not overlap one another, it is possible to separate the frequencies by filtering process after measuring the displacement.

Figure 15:
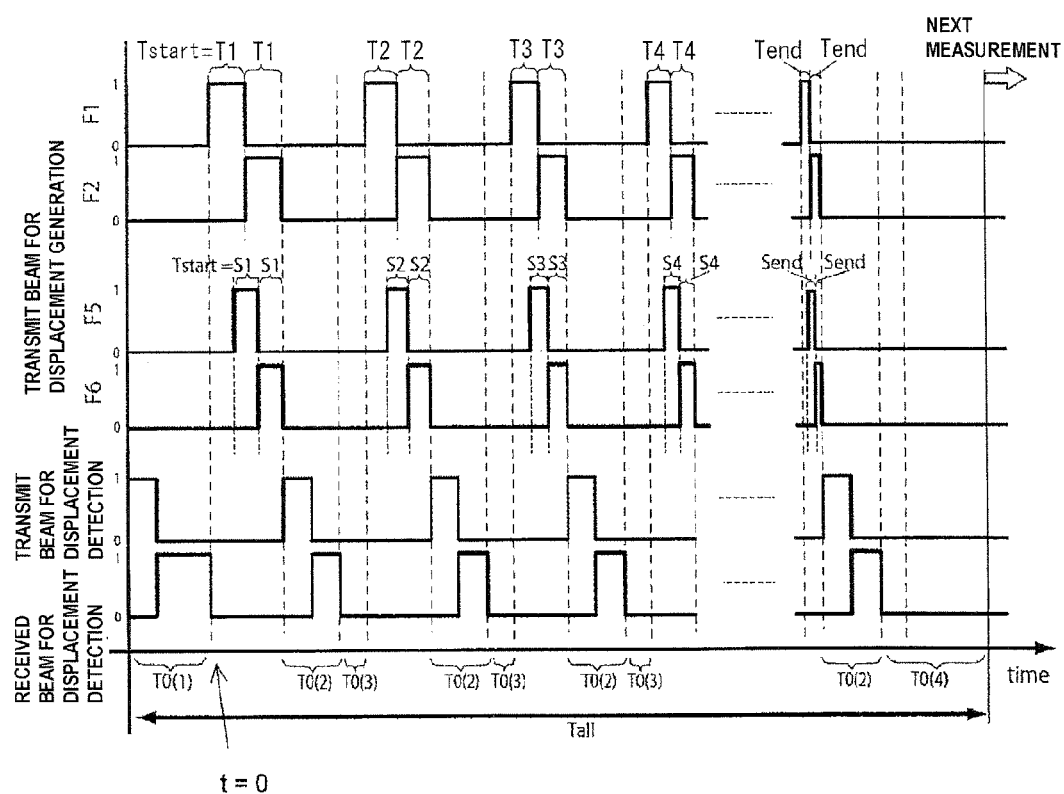
FIG. 15 illustrates a sequence of a method of measurement according to the third embodiment.

On this occasion, the distance between each pair of the focused points is set as the following. By way of example, if it is assumed that the shear wave c is almost the same in both pairs of focused points, when the switching period Sm is N times longer than Tm, the wavelength also becomes N times longer, according to the relationship that the shear wave velocity c=wavelength/switching period (=wavelength*switching frequency). Here, in the case where Sm=N*Tm, if the distance between the focused point F5 and the focused point F6 is set to be N times longer than the distance between the focused point F1 and the focused point F2, it is possible conduct the measurement with the shear wave velocity approximately the same as the shear wave velocity for the focused point F1 and the focused point F2. The time when the focused point F1 and the focused point F2 are ON, and the time when the focused point F5 and the focused point F6 are ON may be the same or may be different. In FIG. 15, the clock time when the focused beam directed to the focused point F2 is switched OFF is set to be the same as the clock time when the focused beam directed to the focused point F5 is switched OFF, thereby allowing the beam for displacement detection to be transmitted immediately after the time of switched OFF.

The direction of the ultrasound beam for displacement detection is controlled to be at an optimum position which allows the two shear waves to be observed. In other words, it is controlled so that the ultrasound beam for displacement detection does not become parallel with any of the proceeding directions of the two shear waves, preferably, to be as orthogonal thereto as possible.

In the flowchart shown in FIG. 10, two pairs of focused points being orthogonal to each other are designated in the step H2, and the distance of one pair of focused points is set to be N times longer than the distance of the other pair. Further in step H3, when the initial value $T_{start}$, the end value $T_{end}$, and the interval $\Delta T$ of the switching period of the time for exposing the two focused points to the focused beam are set, this process automatically sets an initial value $S_{start}$, an end value $S_{end}$, and an interval $\Delta S$ of the switching period, for the pair associated with the N-times longer distance designated in the step H2.

Figure 16:
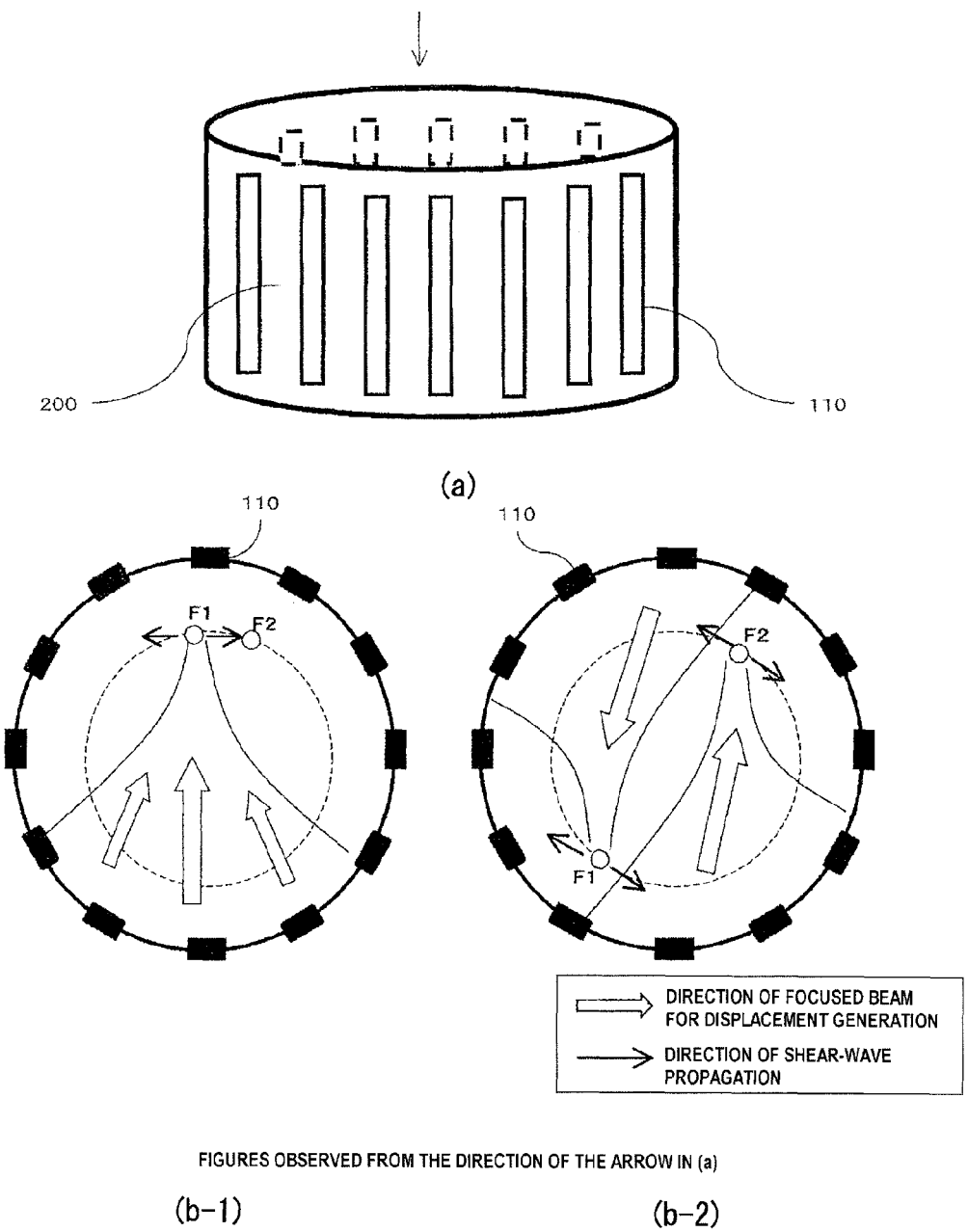
FIG. 16 illustrates the following; (a) is a perspective view of an array probe in the shape of a ring that is used in the third embodiment, and (b-1) and (b-2) illustrate a method of measurement at two focused points by using the array probe.

As a further variation, when the measurement is conducted on a breast portion, it is possible that a ring-like array probe 200 as shown in FIG. 16(a) is placed on the breast portion, instead of the linear array type probe, in such a manner as surrounding the whole circumference of the breast so as to diagnose the hardness thereof. Each probe 110 of the multiple probe elements of the ring-like array probe is arranged on the circumference of the ring-like array probe 200. A delay is electronically added to each probe 110 of the ring-like array probe, thereby allowing focused beam to converge onto an arbitrary position within the test object, being placed inside the ring. With this configuration, it is possible to conceive a method for measuring a value regarding the hardness, as shown in FIG. 16(b-1), for example, by exposing the two different focused points F1 and F2 on a certain circumference within the test object to focused beam. When each focused point is exposed to the focused beam, a group of probes located on the opposite side with respect to the center of the circle is used. This allows more probes to be used than using the probe located closer, and facilitates generation of a desired beam form. In addition, as shown in FIG. 16(b-2), in the case where two focused points are oppositely placed with respect to the center of the circle, the focused beam exposure can be carried out respectively from the opposite directions. Therefore, it is possible to reduce the interference between beams. Accordingly, by using each probe 110 of the ring-like array probe, diagnosis of the hardness along the circumference as shown in FIG. 14 can be conducted more efficiently.

Fourth Embodiment

Figure 17:
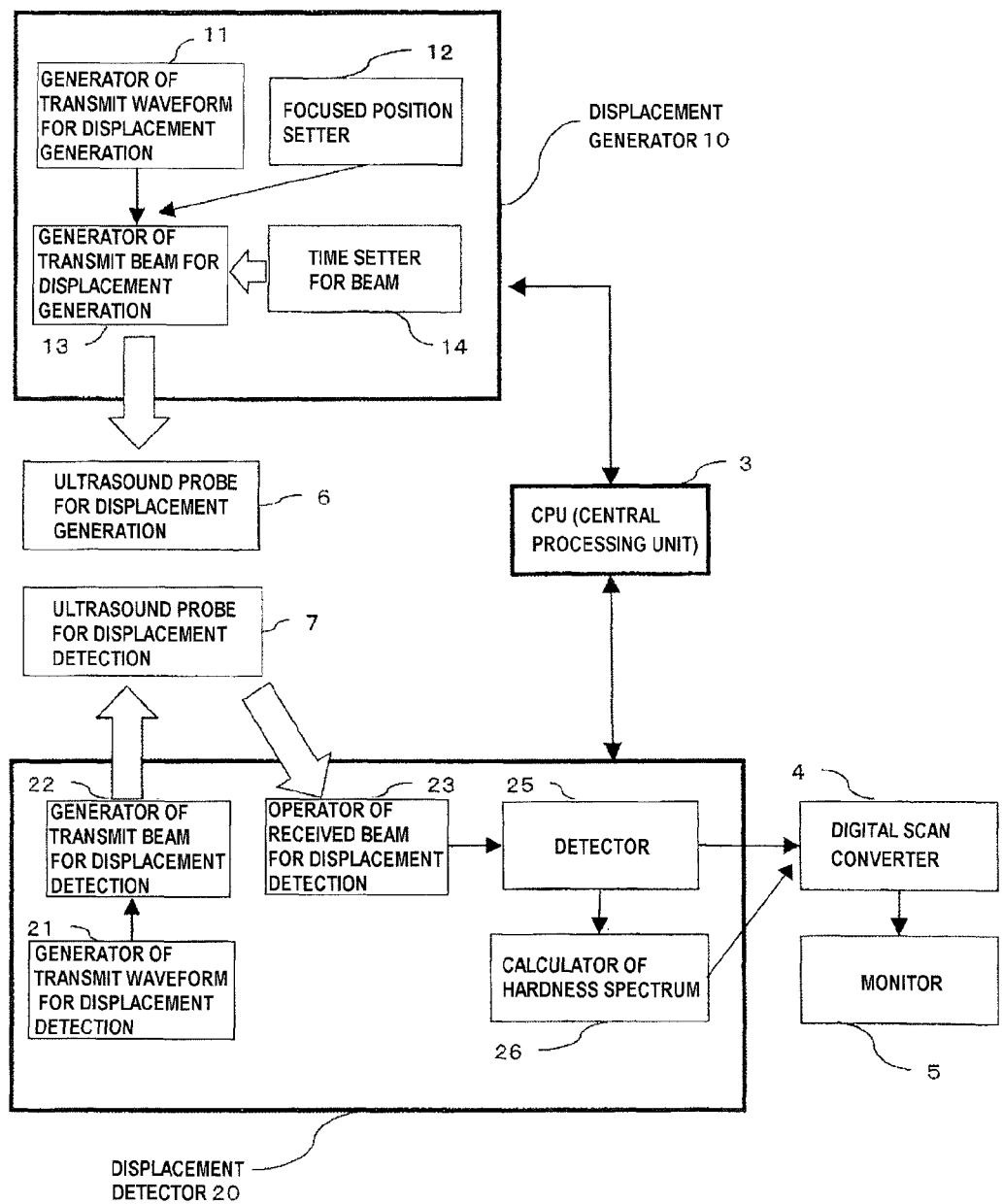
FIG. 17 is a block diagram showing a system configuration of the ultrasonic diagnostic device that uses two ultrasound probes according to a fourth embodiment.
Figure 18:
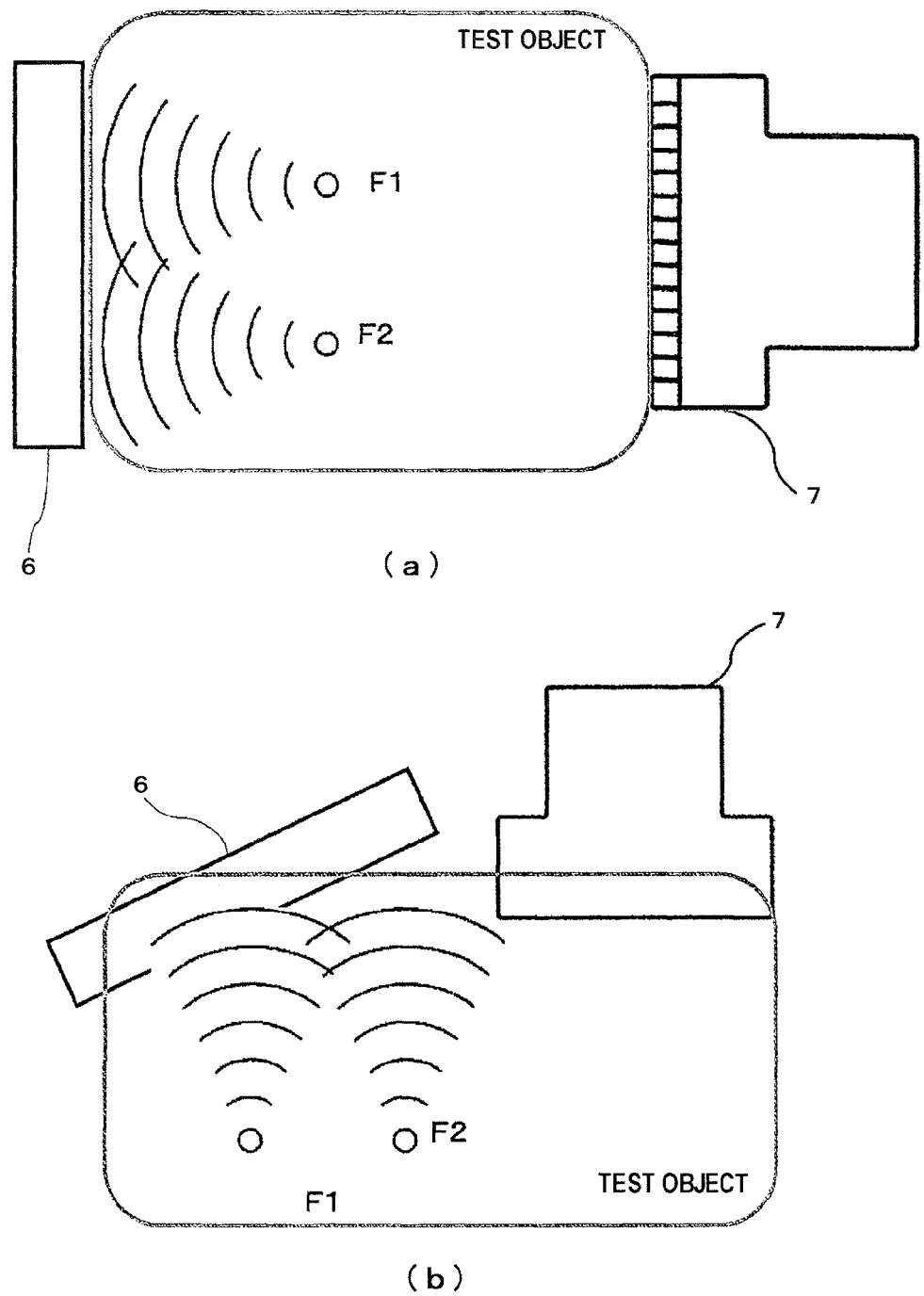
FIG. 18($a$) and FIG. 18($b$) illustrate a method of measurement using the two ultrasound probes according to the fourth embodiment.

With reference to FIG. 17, an explanation will be made as to the fourth embodiment. In the present embodiment, two ultrasound probes respectively for displacement generation and for displacement detection are employed. A position of the probe for transmission and a position of the probe for receiving can be independently moved. In the measurement, as shown in FIG. 18(a), for instance, a test object is placed between the ultrasound probe for displacement generation 6 and the ultrasound probe for displacement detection 7. The ultrasound probe for displacement generation 6 transmits a focused beam and the ultrasound probe displacement detection 7 transmits and receives an ultrasound beam for displacement detection. As shown in FIG. 18(b), it is further possible that the two probes are installed on the body surface of the test object under the condition that the angle between the probes is fixed in advance. As a method of installation and a positional relationship of the two ultrasound probes, an optimum method is employed so as to facilitate detection of a target measurement site and displacement.

Figure 19:
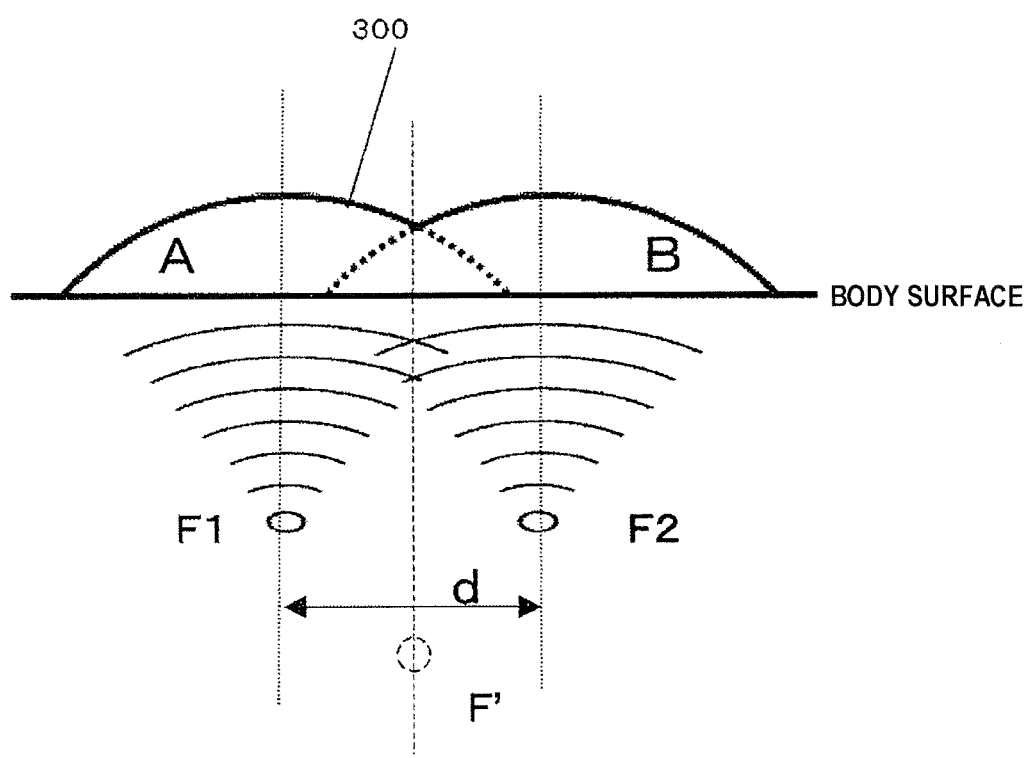
FIG. 19 illustrates a configuration of the front end of the ultrasound transducer of a type that two focused points are fixed, which is applicable in the fourth embodiment.

As the ultrasound probe for displacement generation 6, a linear array type probe may be employed. Furthermore, as shown in FIG. 19, an ultrasound transducer of fixed two-focused point type 300 may be applicable. FIG. 19 shows a cross sectional view of the ultrasound transducer of fixed two-focused point type. The ultrasound transducer of fixed two-focused point type 300 has a structure combining two concave transducers A and B provided with the same curvature (i.e., focal length) and the same aperture diameter, the centers of aperture planes being set apart only by the distance d, in the state where the aperture planes are arranged in parallel. It is to be noted that a part where both transducers are overlapping one another is removed. This configuration enables the following; when the ultrasound transducer of fixed two-focused point type 300 is brought into contact with the body surface, two points on a target cross-sectional plane in the body are exposed to the focused beam, the points being at the same depth from the ultrasound transducer of fixed two-focused point type 300 and being apart only by the distance d in a longitudinal direction (electronic scanning direction) of the ultrasound probe for displacement detection 7. In this example here, at a deeper position than the two focused points within the test object, and on the central axis of the ultrasound transducer of fixed two-focused point type 300, there exists a position where the focused beams are crossing, to which the respective two focused points are exposed. Therefore, if the focused beam directed to the two focused points is switched ON simultaneously, there is a possibility that displacement may occur also on the crossing position F'. In order to avoid this situation, when two concave transducers A and B are assembled, it is possible to bond them, after rotated by the same angle, respectively in the positive direction and in the negative direction with respect to a desired cross-sectional plane. With this configuration, the points where the two focused beams are crossing are in skewed positions, and this enables generation of displacement only at the two focused points. It is to be noted that the distance d between the focused points becomes a smaller value, according to the angle of the rotation, relative to the distance d without any rotation.

The ultrasound transducer of fixed two-focused point type 300 has a fixed distance d between the focused points. Therefore, if it is desired to change the distance, several transducer combinations for the two-focused point type transducer are prepared, and an appropriate transducer is selected and used depending on the site to be diagnosed and conditions thereof.

In the case where the linear array type ultrasound prove is used, positioning of the ultrasound probe for displacement generation 6 with respect to the body surface is electrically controlled to be suitable for the focused points that are set in the focused position setter 12. If the ultrasound transducer of fixed two-focused point type is used, it may be mechanically controlled, or the operator himself utilizes a fixture, a stage or the like, to perform positioning of the ultrasound transducer of fixed two-focused points type.

Here, it is further possible for the operator to determine the two focused points, with reference to a B-mode image taken in advance, or an elastography image taken according to the conventional method, via the input unit (a keyboard, a mouse, a touch panel, or the like), not illustrated. Alternatively, an estimated value being calculated based on a brightness value or a tissue form of the taken image may be set in the focused position setter 12. If the operator himself conducts the adjustment of the focused position, the focused position setter 12 and the process of the step H2 in the flow chart of FIG. 10 may be skipped.

In addition, since the ultrasound probe for wave transmission and the ultrasound probe for wave receiving are separately provided, immediately after a received beam for displacement detection completes scanning the focused position, a next transmit wave beam for displacement generation is allowed to be transmitted, thereby enabling reduction of time. Since there is no passing through the transmit-receive switch 2, it is possible to separate the carrier frequency of the focused beam from that of the transmit-receive wave for displacement detection. Therefore, simultaneously with transmitting the focused beam, the beam for displacement detection can be transmitted and received. With this configuration, the state where the displacement becomes maximum can be monitored, as well as enhancing the frame rate.

The fixed type ultrasound transducer may be a transducer provided with multiple focused points, at least two. However, as the number of the focused points is increased, the acoustic intensity of the focused ultrasound wave at each focused point is decreased for the same input voltage, and the amount of displacement becomes smaller, eventually. In addition to the ultrasound transducer of fixed two-focused point type 300, it is further possible to employ an ultrasound transducer of fixed focused point type with a structure having two focused points in the space within a desired imaging plane. This example excludes an ultrasound transducer having a structure where two focused points are arranged in a line along the longitudinal direction (vertical direction with respect to the body surface).

Fifth Embodiment

Figure 20:
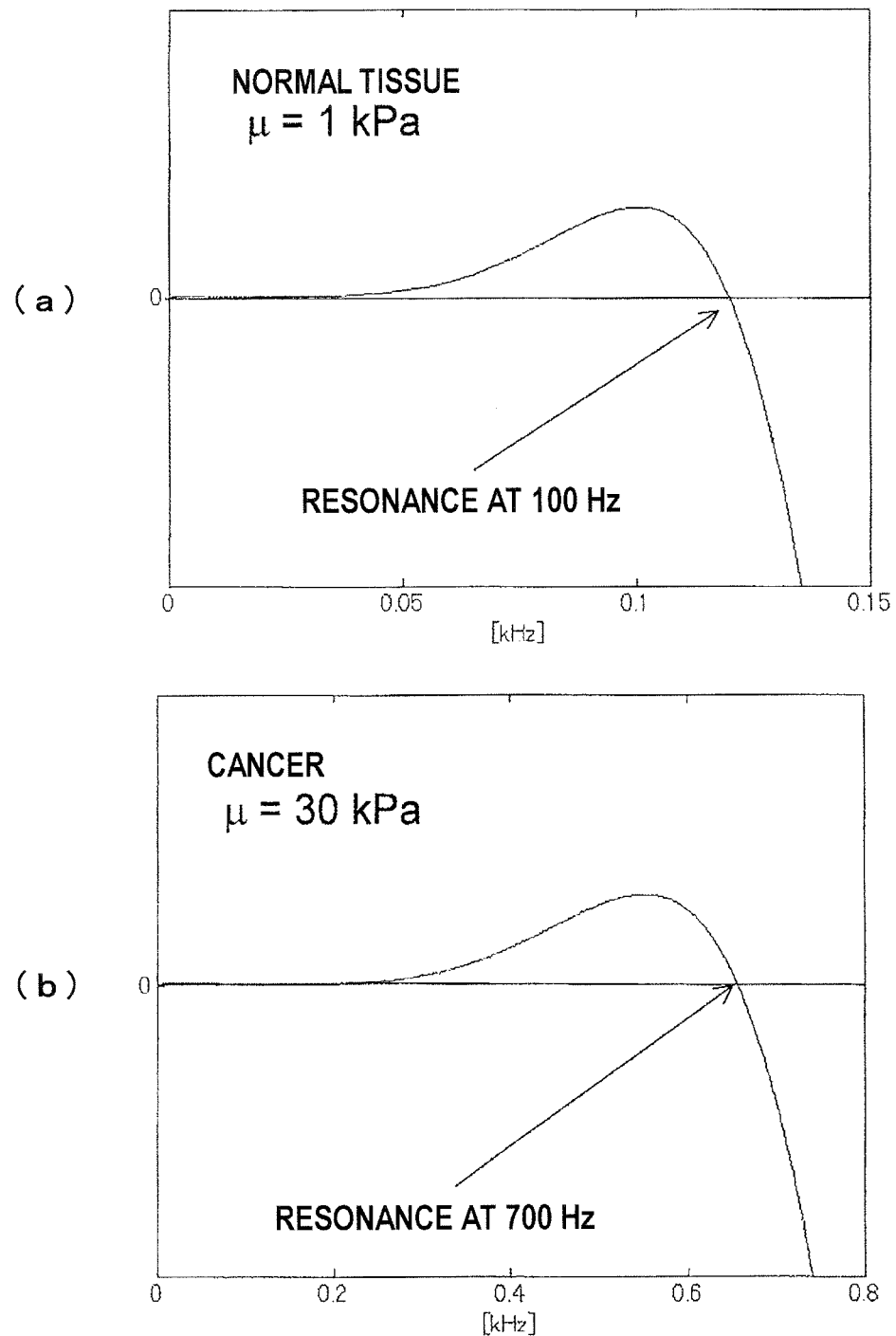
FIG. 20($a$) and FIG. 20($b$) are graphs showing a relationship between a spectrum distribution of a resonance frequency and a natural vibration frequency in the case where the tissue is assumed as being a spherical body, in a fifth embodiment.

In the present embodiment, an explanation will be made as to a method for diagnosing the hardness, based on a resonance frequency, in the case where a tissue like a cancer is assumed as having a spherical body. By way of example, an intrinsic resonant frequency of the spherical body with respect to a shear wave elastic modulus $\mu$ has a spectrum distribution as shown in FIG. 20 (Non Patent Document 3). In the case where the frequency crossing zero on the vertical axis in the figure is assumed as the resonance frequency, when the shear wave elastic modulus of the cancer ($\mu$=30) is 30 times larger than that of the normal tissue ($\mu$=1), it is found that the resonance frequency becomes approximately 7 times larger.

Figure 21:
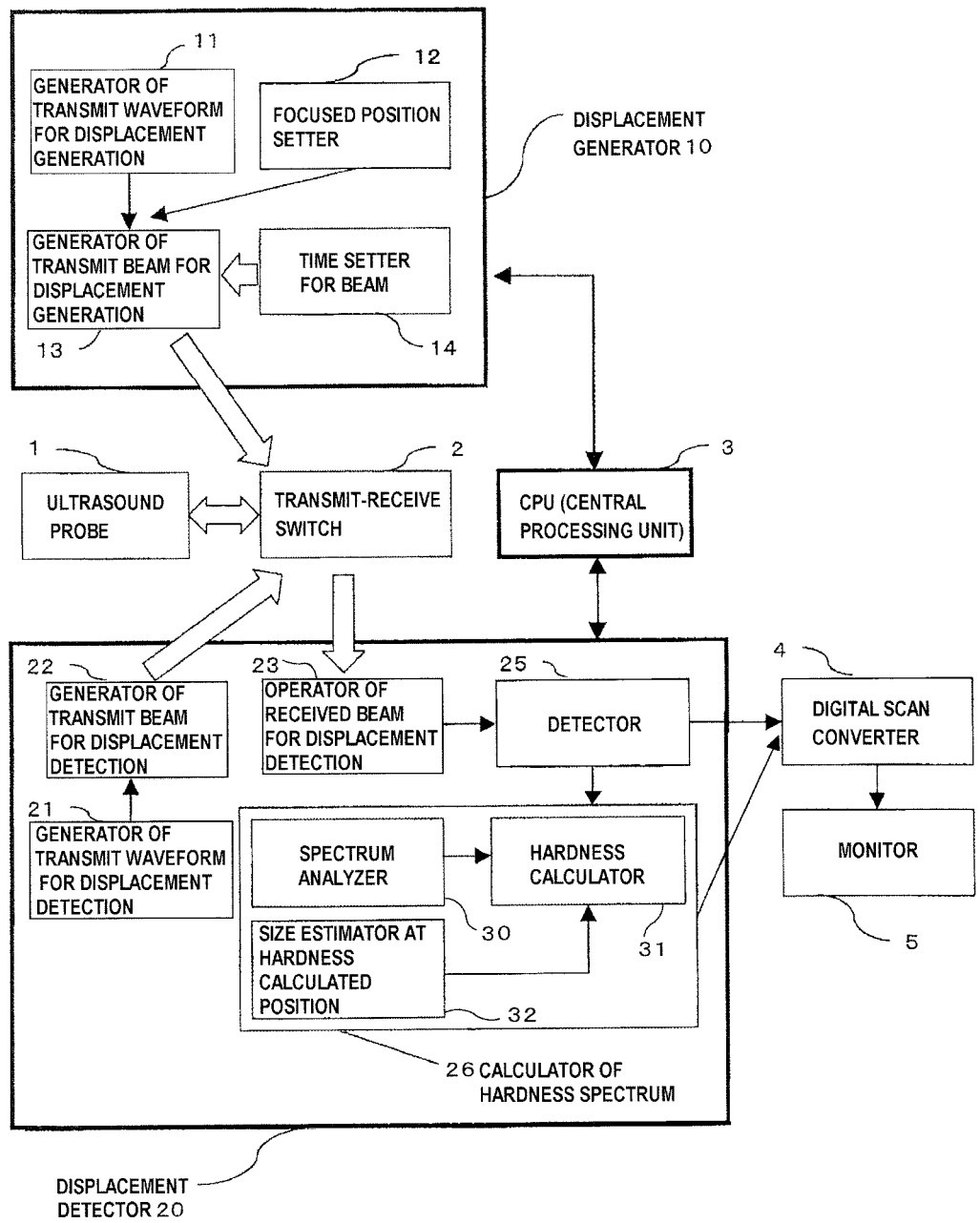
FIG. 21 is a block diagram showing a system configuration of the ultrasonic diagnostic device according to the fifth embodiment.

FIG. 21 is a system block diagram showing the present embodiment. The present embodiment is different from the first embodiment, in the point that the calculator of hardness spectrum 26 incorporates a spectrum analyzer 30, a size estimator at hardness calculated position 32, and a hardness calculator 31. When diagnosis is conducted based on the resonance frequency from the spherical body, the size estimator at hardness calculated position 32 obtains by using an imaging process, a radius r of the sphere, from a B-mode image or an elastography image taken by the conventional method. It is alternatively possible for the operator to input the radius r. After the spectrum analyzer 30 analyzes a switching frequency $f_M$ showing a peak value, the hardness calculator 31 calculates a value of the hardness, such as the shear wave elastic modulus based on the radius r and the switching frequency $f_M$. The radius r being estimated in the size estimator at hardness calculated position 32 is displayed in the monitor 5, as a numerical value or in the form of circle having the radius r, and in addition, the peak frequency and the shear wave elastic modulus are also displayed.

The explanation above has been made as to the spherical body, but it is further possible to use an intrinsic resonant frequency of a shape that is optimum for a diagnostic site, such as a circle, an ellipsoidal body, and a ring.

Hereinafter, a time required for the measurement will be discussed, with regard to the embodiments described above.

Figure 22:
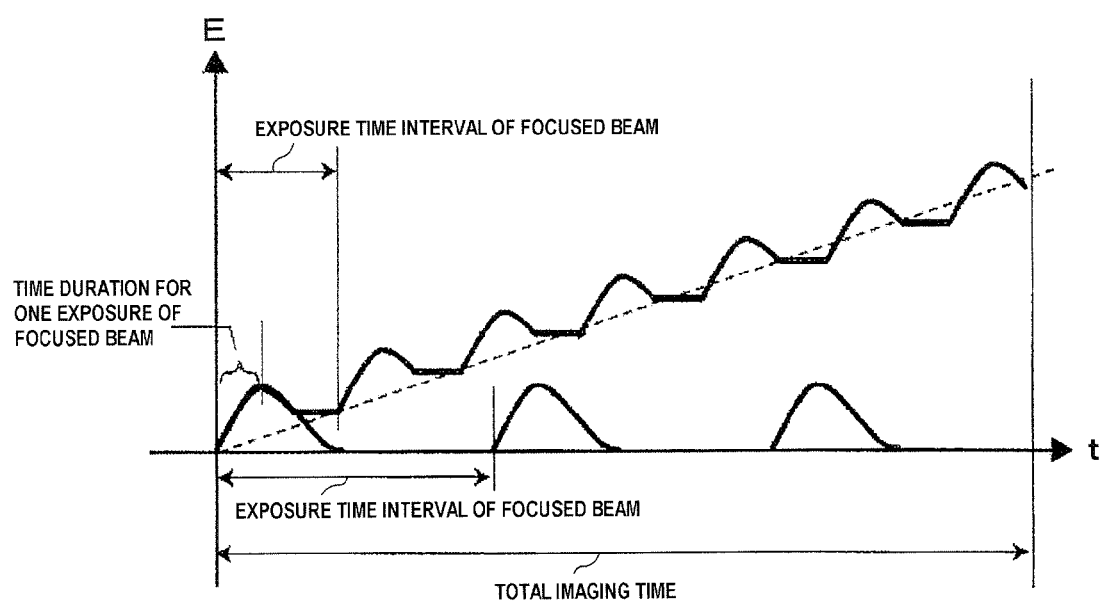
FIG. 22 illustrates a graph showing a relationship between the total imaging time and a rise in temperature in the fifth embodiment.

As shown in FIG. 22, a rise in temperature within the test object depends on the time duration for exposure of the focused beam, and an exposure time interval thereof. Even though the acoustic intensity is the same, a percentage of rise in temperature becomes larger, as the time duration for one exposure of the focused beam according to the burst-chirp method is longer and the time interval of multiple focused beam exposures is shorter. In order to maintain the safety in the living body, the time duration for exposure and the exposure time interval are controlled so that the maximum rise in temperature becomes lower than 1° C.

A rise in temperature will be considered, in the case where the beam is transmitted according to the burst-chirp method in the switching period from hundreds of microseconds to several milliseconds. By way of example, according to a calculation based on a coefficient of thermal conductivity of a living body, the maximum rise in temperature is estimated to be around 0.1° C., when the acoustic intensity is 1 kW/cm$^2$, the attenuation rate of the living body is 0.5 dB/cm/MHz, and the time duration for exposure is 1 ms. In addition, according to a result of the calculation, the time from the maximum rise in temperature until returning to the temperature in the initial state before the exposure of the beam (relaxation time) is approximately 5 s. Therefore, in order to maintain the safety against the temperature, either of the followings is necessary to conduct the measurement; to constantly keep the time interval to 5 s or longer, from the end of the beam transmission according to the burst-chirp method directed to a certain pair of focused points, until the start time for transmitting the next burst-chirp signal to the same pair of the focused points, or to transmit the burst-chirp signal for multiple number of times until when the rise in temperature becomes 1° C. This will be explained in the following, taking the illustration of FIG. 5 as an example, which describes the first embodiment. In this example here, it is assumed that acquisition of the reference signal is performed only for the initial one time.

Here, it is also assumed that the time duration for exposure of the burst-chirp signal is TB, the transmit-receive time of the beam for displacement detection is T0(2), the time after transmitting the beam for displacement detection until the exposure of the next burst-chirp signal is T0(3), and the time from the end of receiving the last beam for displacement detection to the next time of measurement (waiting time) is T0(4).

Firstly, the case where the measurement is conducted at one pair of focused points will be discussed. In order to make the measurement time to be the shortest, T0(3) is set to be 0. On this occasion, m, being the number of Tm is determined by 1° C./(temperature rise E1 by one-time beam exposure). Therefore, when E1 is 0.1° C., m=10. If each of all the followings; T0(1), TB+T0(2), and the time for acquiring a cross-sectional image in the step H7 of FIG. 10 is approximately 10 ms, the measurement is completed by (10+10*10+10)=120 ms. On this occasion, the frame rate becomes 1/120 ms=8 Hz. It is to be noted that since the temperature rises approximately by 1° C. after the measurement, the state comes into a waiting state (T0(4)=approximately 5 seconds) without starting the next measurement, until the temperature falls to the original. Other site may be measured while the waiting time.

If it is considered the safety is important, T0(3) is set to 5 seconds and this allows the temperature to become the same temperature at the time of starting the measurement. Therefore, m can be determined irrespective of the rise in temperature. On this occasion, the measurement time is almost proportional to m. For example, if m=5, the measurement time is 5*5=25 seconds and the frame rate becomes 0.04. In addition, a subsequent measurement can be conducted, even though the waiting time is not provided.

T0(3) is settable within the range from 0 to 5 seconds. If T0(3) becomes smaller, the measurement time becomes shorter, but the number of Tm is limited and the waiting time becomes longer. On the other hand, if T0(3) is larger, the number of measurable Tm is increased and the waiting time becomes shorter, but the measurement time becomes longer.

Hereinafter, the case where multiple pairs of focused points are scanned for conducting the measurement will be discussed. It is assumed that the number of pairs of focused points is 10. If it is also assumed that T0(3)=0, the time is (10+10*10*10+10)=1,020 ms for one pair of focused points described above. On this occasion, the frame rate is 0.1. On the other hand, when T0(3)=5 seconds, if a rise in temperature in each pair of focused points has no impact on the other pairs of focused points, it is possible to conduct measurement on multiple pairs during the time T0(3). Therefore, the frame rate is the same as the frame rate when the measurement is performed at one pair of focused points.

Upon measurement, information items such as the acoustic intensity, the maximum rise in temperature, relaxation time, and a region of temperature rise, with respect to the parameters such as TB and T0(3), are stored in a recording medium not illustrated, and the CPU (Central Processing Unit) 3 controls so that an optimum measurement is carried out at an optimum frame rate. A screen display or a sound may notify the operator that the waiting time has started. In the step H3 of FIG. 10, it is additionally possible to display a time required for measurement, a settable number of Tm, the waiting time, Tall=(time required for measurement+waiting time), and the like.

Figure 23:
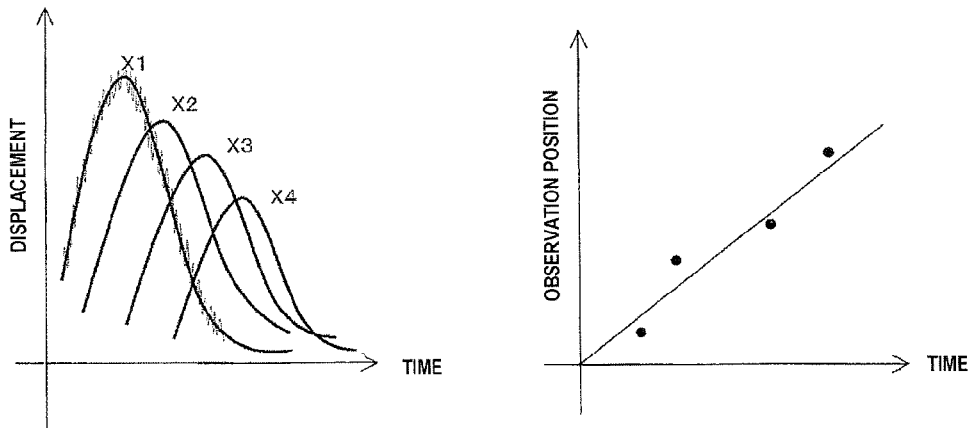
FIG. 23 illustrates the following; (a-1) shows that one focused point is exposed to a focused beam to deform the tissue, indicating a relationship between the displacement and time, measured at multiple positions (X1, X2, X3, X4), (a-2) is a graph showing a straight line linearly approximating the relationship between the time when the displacement reaches a peak and each observation position, (b-1) illustrates the observation points A and B in the case where two focused points are exposed to the focused beam in the fifth embodiment, (b-2) is a graph showing a relationship between the displacement of the observation points A and B, and the time, and (b-3) illustrates an absolute value of displacement and a direction of shear-wave propagation as to each observation position.
Figure 23:
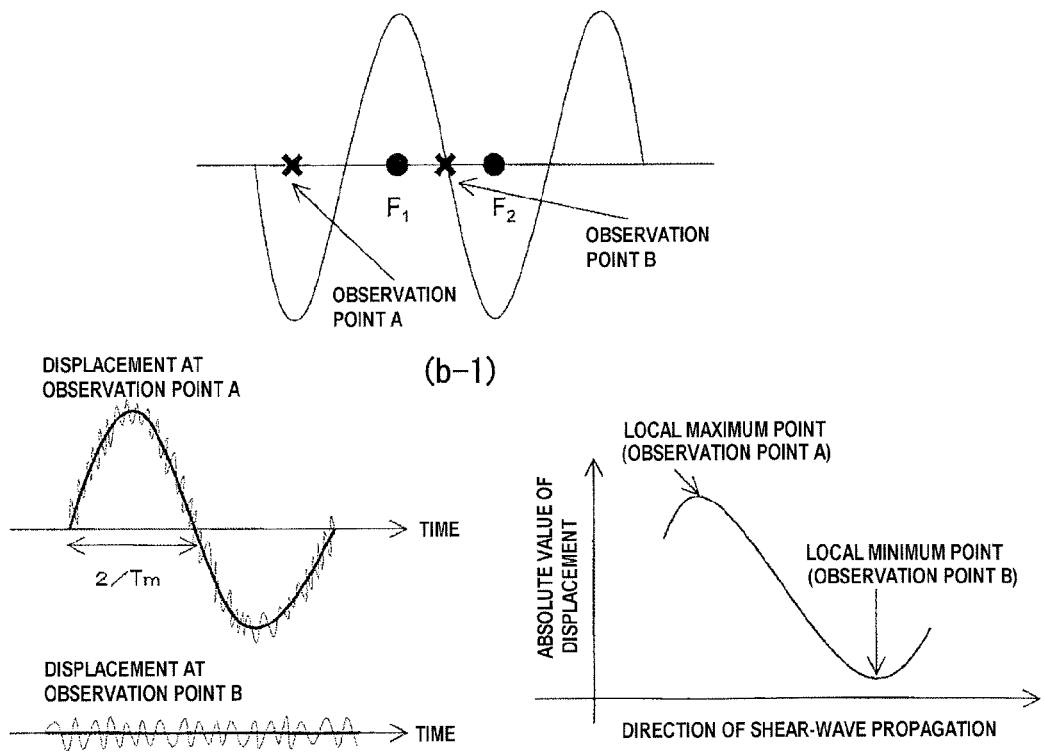

Next, an error in the hardness measurement will be discussed. FIGS. 23(*a*-1) and (a-2) illustrate a method for exposing one focused point to a focused beam for deforming the tissue, measuring displacement of a shear wave being produced, at equally-spaced multiple positions (e.g., X1, X2, X3, and X4) in the propagation direction of the shear wave, and deriving the relationship between the displacement and the time. In this method, as shown in FIG. 23(*a*-2), it is possible to estimate the shear wave velocity c, from a gradient of a straight line obtained by linearly approximating the relationship between the time when the displacement reaches a peak, and each observation position. On this occasion, there exists a noise indicated by the dotted line on the displacement waveform, and it causes an error when a peak value is obtained. In order to minimize the error, it is conceivable that the sampling frequency is made higher, and data as much as possible is used when the peak value is calculated. However, this method restricts data of waveform signals usable in the operation for obtaining the peak value, to the data in proximity to the peak value. As an alternative, there is a method for perform fitting for all over the waveform. In this case, however, even though data of the entire displacement waveform is usable, the shape of the displacement waveform has to be presupposed, and there is a possibility of deviation of the peak position. In addition, if a noise of the displacement waveform is removed by a low-pass filter, the waveform itself is deformed, and therefore, there is a possibility that the peak position may deviate anyway.

Next, with reference to FIGS. 23(*b*-1), (b-2), and (b-3), an explanation will be made as to an error in the burst-chirp method for two focused points, suggested by the present embodiment. By way of example, in FIG. 23(*b*-1), during a certain switching period Tm, the absolute value of displacement becomes a local maximum value at the observation position A, and the absolute value of displacement becomes a local minimum value at the observation position B (FIG. 23(*b*-2)). In the case where monitoring is conducted at multiple observation points in the shear wave displacement direction, the absolute values of displacement for the respective observation positions form a curve as shown in FIG. 23(*b*-3), for instance. As mentioned above, when the switching period Tm is made to change, the shear wave velocity is estimated based on the switching period $T_M$ showing the peak of the absolute value of displacement (FIG. 7(*a*)). In this method, as shown in FIG. 23(*b*-2), a noise exists as indicated by the dotted line on the displacement waveform, causing an error in calculating the local maximum value. Here, in order to remove the noise, it is possible to calculate an integration value of the absolute values of displacement. By way of example, the integration value for the observation point A is a value not zero, whereas the integration value for the observation point B is nearly zero. In this integration operation, all the wave signal data is usable, and it is not necessary to consider variations of the waveform, or the like. Therefore, in the suggested method, measurement of hardness can be conducted using much more data relative to the method shown in FIGS. 23(*a*-1) and (a-2), thereby diminishing the error.

A two-dimensional probe maybe employable instead of the linear array type probe, in all the embodiments described above. In addition, as the probe, a ceramic probe, a polymer probe, a semiconductor probe may be used, but the probe is not limited to those examples.

Industrial Applicability

The present invention is applicable to the field of an ultrasound system.

Explanation Of References

1 . . . ULTRASOUND PROBE, 2 . . . TRANSMIT-RECEIVE SWITCH, 3 . . . CPU (CENTRAL PROCESSING UNIT), 4 . . . DIGITAL SCAN CONVERTER, 5 . . . MONITOR, 10 . . . DISPLACEMENT GENERATOR, 11 . . . GENERATOR OF TRANSMIT WAVEFORM FOR DISPLACEMENT GENERATION, 12 . . . FOCUSED POSITION SETTER, 13 . . . GENERATOR OF TRANSMIT BEAM FOR DISPLACEMENT GENERATION, 14 . . . TIME SETTER FOR BEAM, 20 . . . DISPLACEMENT DETECTOR, 21 . . . GENERATOR OF TRANSMIT WAVEFORM FOR DISPLACEMENT DETECTION, 22 . . . GENERATOR OF TRANSMIT BEAM FOR DISPLACEMENT DETECTION, 23 . . . OPERATOR OF RECEIVED BEAM FOR DISPLACEMENT DETECTION, 25 . . . DETECTOR, 26 . . . CALCULATOR OF HARDNESS SPECTRUM, 30 . . . SPECTRUM ANALYZER, 31 . . . HARDNESS CALCULATOR, 32 . . . SIZE ESTIMATOR AT HARDNESS CALCULATED POSITION, 100 . . . EACH DEVICE OF ULTRASOUND PROBE 1, 110 . . . EACH PROBE OF RING-LIKE ARRAY PROBE, 200 . . . RING-LIKE ARRAY PROBE, 300 . . . ULTRASOUND TRANSDUCER OF FIXED TWO-FOCUSED POINT TYPE

What is claimed is:

1. An ultrasonic diagnostic device comprising,
an ultrasound probe for transmitting a focused beam toward each of multiple focused points in a tissue of a living body to generate displacement of the tissues at focused points, thereby producing multiple shear waves, then transmitting a beam for displacement detection toward a displacement detector point where interference between the shear waves is caused for detecting the displacement of the tissue according to the shear wave, and receiving an echo signal of the beam for displacement detection from the living body;

a focused point setter for setting the focused points, and the displacement detector point wherein interference between the shear waves is caused; and a displacement detector for detecting the displacement of the tissue at the displacement detector point according to the shear wave from the echo signal, and estimating a shear wave velocity based on the displacement of the tissue.

2. The ultrasonic diagnostic device according to claim 1, further comprising:
   a time setter for transmit beam for setting a time to transmit the focused beam.

3. The ultrasonic diagnostic device according to claim 1, further comprising:
   a displacement detector for calculating hardness of the tissue based on the echo signal.

4. The ultrasonic diagnostic device according to claim 3, further comprising:
   a monitor for displaying the hardness being calculated.

5. The ultrasonic diagnostic device according to claim 2, wherein the time setter for transmit beam set the transmit time in such a manner that a switching period for switching the focused beam between ON and OFF is the same for the multiple positions being different.

6. The ultrasonic diagnostic device according to claim 2, wherein the time setter for transmit beam sets the transmit time in such a manner that a switching period for switching the focused beam between ON and OFF is different for the multiple positions being different.

7. The ultrasonic diagnostic device according to claim 5, wherein the time setter for transmit beam sets the transmit time with temporal variation, so that at least one switching period for the multiple positions serves as either of a periodic chirp signal and a phase chirp signal.

8. The ultrasonic diagnostic device according to claim 6, wherein the time setter for transmit beam sets the transmit time with temporal variation, so that at least one switching period for the multiple positions serves as either of a periodic chirp signal and a phase chirp signal.

9. The ultrasonic diagnostic device according to claim 1, wherein the number of the multiple positions being different is two.

10. The ultrasonic diagnostic device according to claim 1, wherein the time setter for transmit beam operates to expose the multiple positions to the focused beam simultaneously.

11. The ultrasonic diagnostic device according to claim 1, wherein the time setter for transmit beam operates to expose the multiple positions to the focused beam alternately.

12. The ultrasonic diagnostic device according to claim 1, wherein the multiple focused points are variable with respect to the ultrasound probe.

13. The ultrasonic diagnostic device according to claim 1, wherein the multiple focused points are located at a distance more than a beam width of the focused beam at the focused point, and less than a propagation distance of the shear wave being detectable.

14. An ultrasonic diagnostic device comprising:
   a first ultrasound probe for transmitting a focused beam toward each of multiple focused points in a tissue of a living body to generate displacement of the tissue at the focused points, thereby producing multiple shear waves;
   a second ultrasound probe for transmitting a beam for displacement detection toward a displacement detector point where interference between the shear waves is caused for detecting the displacement of the tissue according to the shear wave, and receiving an echo signal of the beam for displacement detection from the living body;
   a focused point setter for setting the focused points, and the displacement detector point where interference between the shear waves is caused; and
   a displacement detector for detecting the displacement of the tissue at the displacement detector point according to the shear wave from the echo signal, and estimating a shear wave velocity based on the displacement of the tissue.

15. An ultrasonic diagnostic device being connectable with a beam generator for displacement detection, for transmitting a beam for displacement detection to detect displacement in a tissue of a living body, comprising;
   an ultrasound probe for transmitting a focused beam toward each of multiple focused points in the tissue of the living body to generate displacement of the tissue at the focused points, thereby producing multiple shear waves, and receiving an echo signal of the beam which is transmitted by the beam generator toward a displacement detector point where interference between the shear waves is caused;
   a focused point setter for setting the focused points, and the displacement detector point where interference between the shear waves is caused; and
   a displacement detector for detecting the displacement of the tissue at the displacement detector point according to the shear wave from the echo signal, and estimating a shear wave velocity based on the displacement of the tissue.

* * * * *